US005776179A

United States Patent [19]

Ren et al.

[11] Patent Number: 5,776,179

[45] Date of Patent: Jul. 7, 1998

[54] METHOD FOR EVALUATING INNER EAR HEARING LOSS

[75] Inventors: Tianying Ren; Alfred L. Nuttall, both of Ann Arbor, Mich.

[73] Assignee: The University of Michigan, Ann Arbor, Mich.

[21] Appl. No.: 539,821

[22] Filed: Oct. 6, 1995

[51] Int. Cl.$^6$ .................................................. A61N 1/00

[52] U.S. Cl. ............................ 607/137; 607/55; 607/56; 607/57

[58] Field of Search .................................. 607/137, 116, 607/55–57; 128/746, 898; 600/25, 559; 623/10

[56] References Cited

U.S. PATENT DOCUMENTS 4,535,785 8/1985 van den Honert et al. ............ 128/746

OTHER PUBLICATIONS

*Electrically Evoked Otoacoustic Emissions from the Apical Truns of the Gerbil Cochlea*, Hideko H. Nakahima, et al., Acoustical Society of America, pp. 786–794, 1994.

Meausurement of Otoacoustic Emissions for Hearing Assessment, M.L. Whitehead et al., IEEE Engineering in Medicine and Biology, pp. 210–226, 1994.

*Alternating Current Delivered into the Scala media Alters Sound Pressure at the Eardrum*, Allyn E. Hubbard et al., American Association for the Advancement of Science, vol. 222, pp.510–512, 1983.

*Acoustic Enhancement of Electrically–Evoked Otoacoustic Emissions Reflects Basilar Membrane Tuning: Experiment Results*, Shuwan Xue et al., Hearing Research, pp. 121–126, 1993.

*Alternating Current Induced Otoacoustic Emissions in the Guinea Pig*, Keiichi Murata et al., Hearing Research, pp. 201–214, 1991.

*Electrophonic Hearing and Cochlear Implants*, Arne Risberg, et al., Acta Otolaryngol (Stockh), pp. 156–163, 1990.

*Das "Radiophon"*, Dr. Gustav Eichhorn, pp. 308–312.

*Primary Examiner*—John P. Lacyk
*Assistant Examiner*—Rosiland Kearney
*Attorney, Agent, or Firm*—Wells, St. John, Roberts, Gregory & Matkin P.S.

[57] ABSTRACT

A method for evaluating the electromotility of hair cells within the cochlea of a mammalian ear by providing an electrode in proximate relation with the round window and applying electricity therethrough in order to electrically excite hair cells within the cochlea to produce electrically-evoked otoacoustic emissions therefrom. The electrically-evoked otoacoustic emissions further excite the internal structure of the cochlea which produces vibrations at the oval window that act through the bones of the middle ear to drive the tympanic membrane, producing corresponding acoustic sounds in the ear canal. The resulting acoustic sounds in the ear canal are subsequently detected with a microphone where they are later measured and characterized via readily available signal processing techniques. A hearing aid device is also provided by this invention utilizing the features of the before mentioned analysis technique wherein a traditional hearing aid device acoustically captures a sound adjacent the outer ear and converts it to an electrical signal which is fed to the electrode in order to excite the hair cells within the cochlea and produce electrically-evoked pressure waves therein. The resulting electrically-evoked pressure waves subsequently excite the cochlea and produce perceived hearing in the brain of the test subject through the normal hearing processes of hair cells and conducting neurons.

21 Claims, 19 Drawing Sheets

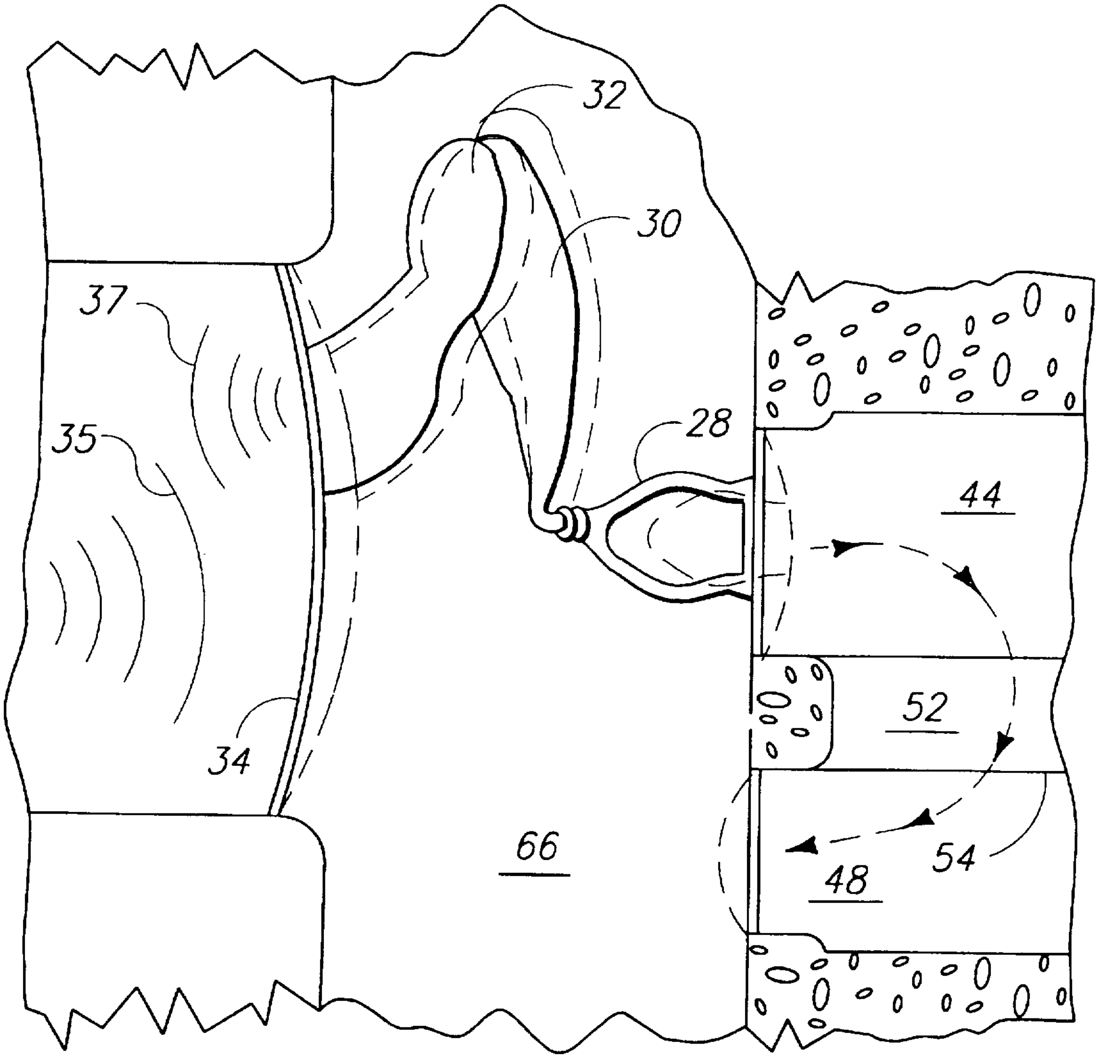
Fig 7-A

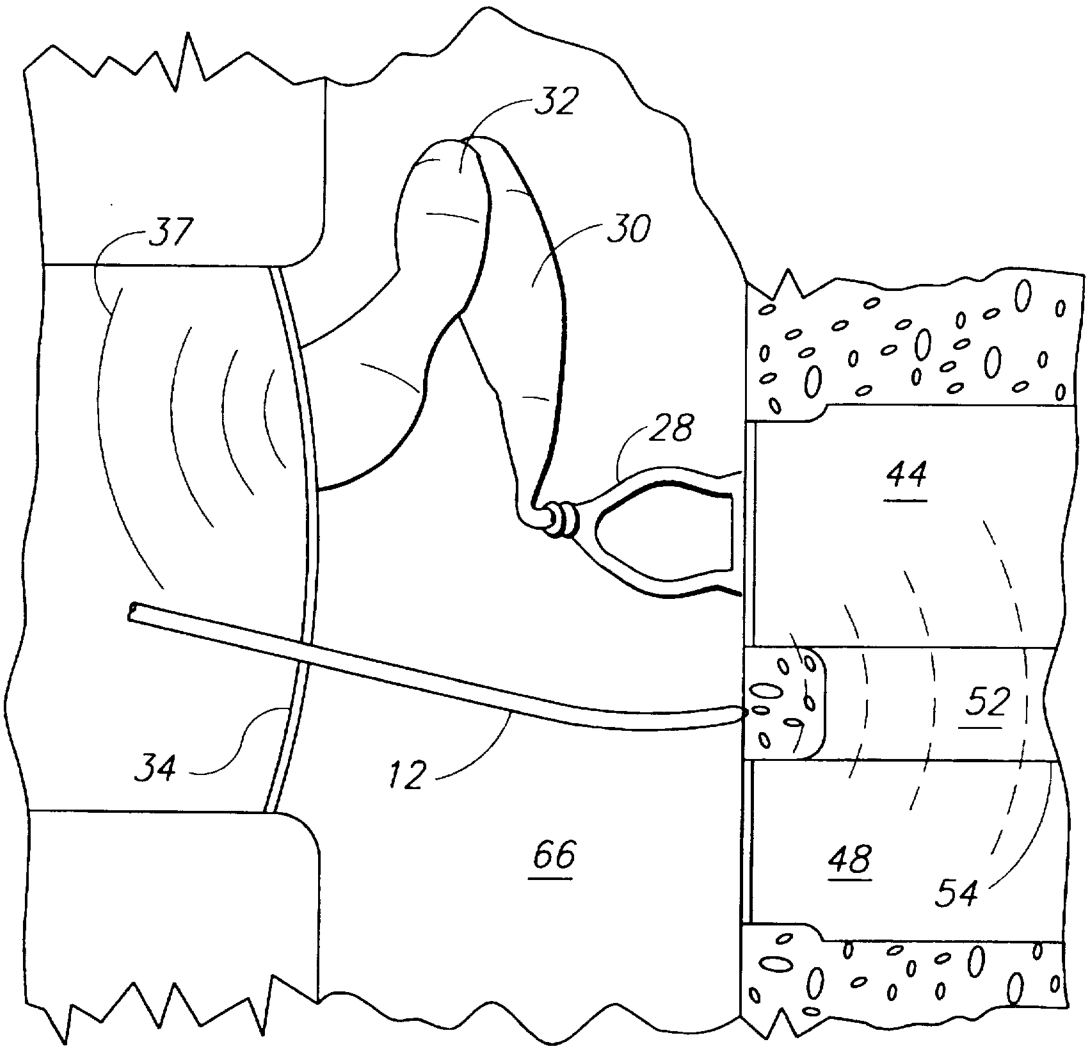
Fig 7-B

METHOD FOR EVALUATING INNER EAR HEARING LOSS

GOVERNMENT SUPPORT

The invention was made at least partially with Government support under Contract No. NIH NIDCD 5 R01 DC00141-15 under the title "Method for Evaluating Inner Ear Hearing Loss and Apparatus for Assisting Restoration of Hearing". The Government has certain rights in this invention.

TECHNICAL FIELD

This invention relates to conditions of hearing loss occurring in a mammalian ear, and more particularly to a diagnostic method for measuring electromotile health of outer hair cells in a cochlea; and a hearing aid utilizing an electrode configured to effect electromotile hearing within the cochlea, wherein the electrode is driven by an electric signal received from a hearing aid positioned either in the outer ear or externally of the ear.

BACKGROUND OF THE INVENTION

There are a number of previously known devices for detecting hearing loss in individuals. Additionally, there are a number of different hearing aids that operate to partially or completely recover hearing loss resulting from one or more physiological changes that can occur within an ear, or to produce acceptable hearing for the first time in cases of congenital defect.

Some previously known methods for evaluating hearing loss in an individual have involved the application of electric current to the test subject, typically to impart hearing in the subject by provoking auditory sensations. Under normal acoustical stimulation of the tympanic membrane, the auditory energy drives the inner ear via the normal mechanical features of the middle ear to produce pressure waves within the inner ear, resulting in sensory cell and neural activity therein.

Alessandro Volta a 17th Century Italian physicist is thought to be the first to apply current to the human head. In early first attempts, Volta applied electrical current to his own head.

In the early 20th Century, leading up to the 1950's and 1960's, there was a significant increase in activity in both the United States and Russia in an effort to determine the mechanisms by which application of electric current leads to auditory sensations. At this time, a German device called the "Radio Phon" received a patent D.R.P.N.R. 461,711 on May 13, 1927. The device acted like a telephone receiver and in use was placed on the side of a user's head to apply electric currents therealong, leading to auditory sensations. However, these early attempts all involved the production of auditory sensations largely from vibrations of the skin caused directly by application of the electric current. In these cases, vibration of the outer skin produces acoustic sounds that are perceived by the listener through one of two mechanisms: either through bone conduction, or through air conduction in combination with the normal air-conduction path extending from the external ear canal to the inner ear.

More recent studies have subsequently concluded that a portion of the hearing experienced by individuals in the previously mentioned tests resulted when electric current stimulation was applied directly to the inner ear itself. Recently, it has been suspected that the currents directly stimulate either the hair cells or the auditory nerves.

One recent investigation has involved studying the phenomena of ear canal sounds or otoacoustic emissions caused by the application of electric current stimulation. This recent investigation, as well as a number of similar studies have involved the application of a specialized micro-glass electrode which is drawn to a fine point and inserted into the scala media of the inner ear. However, this surgical technique is difficult to perform and the approach is technically complex and is invasive to the inner ear which does not make the method feasible for use in humans, nor is it even a convenient method for studying hair cell activity in animal subjects. Following placement of the electrode into the scala media, an electrical stimulus is input at a selected frequency and resulting ear canal sounds are measured.

Another procedure involves the simultaneous application of an acoustic stimulus and an electrical stimulus which leads to distortion products between the stimuli as a result of non-linear processes in the inner ear. A most recent study by Mountain and Hubbard has investigated the first-order, sum and difference intermodulation distortion tones resulting from such stimulation. Murata et al., Alternating Current Induced Otoacoustic Emissions in the Guinea Pig, Hearing Research pp. 55, 201–204, 1991 has further confirmed these earlier results by injecting current in guinea pig cochleas and then measuring ear canal sounds. Similarly, the Murata et al. technique uses the scala media microelectrode-based technique for injecting electric current into the inner ear. However, the scala media electrode position is risky and difficult as it is an invasive procedure to the cochlea. Therefore, a risk of infection as well as potential injury to the inner ear are both present.

A widely used diagnostic tool for assessing levels of hearing loss involves measurement of otoacoustic emissions from within the outer ear canal. In this technique, acoustic stimulus tones are delivered into the outer ear canal through a pair of delivery tubes where they stimulate the tympanic membrane and, then the ossicle chain in the middle ear. The stimuli produce corresponding pressure waves in the fluids of the inner ear and a basilar membrane displacement wave. The nonlinearity of the active process in the organ of Corti creates travelling waves of audio-frequency vibration energy within the cochlea which follow the acoustic pathway in a reverse direction. Hence, vibrations are produced at the ear drum such that the ear drum acts as a speaker to produce faint acoustic sounds in the outer ear canal. These acoustic sounds are then recorded with the use of an ear-canal microphone. Such a technique has been reviewed recently by M. L. Whitehead et al., Measurement of Otacoustic Emissions for Hearing Assessment, IEEE Engineering in Medicine and Biology, pp. 210–266, April/May 1994.

However, the above mentioned technique requires delivery of an audible stimulus in the outer ear canal acting on the tympanic membrane, the bones of the middle-ear, the fluids inside the cochlea, and the sensory cells. The ear canal sounds, the otoacoustic emissions, and the distortion products are strongly dependent on the normal active nonlinear processing of the organ of Corti. The presence of such nonlineary is independent of the presence of outer hair cells. There is a need to provide a technique which directly produces otoacoustic emissions by application of an electric stimulus such that the resulting otoacoustic emissions can be monitored in order to detect the physiological condition of the inner ear. This needs to be accomplished in a noninvasive manner avoiding the risky procedure of invasively entering the inner ear with a microelectrode.

Another area of endeavor has involved the development of hearing aids. One previously known device for enhancing hearing loss in an individual involves the use of a microphone and amplifier to collect acoustic sounds from a location adjacent the outer ear, or pinna, after which the signal is amplified and modified and directed into the outer ear canal. The delivered signal drives the tympanic membrane and the middle ear bones to impart fluid pressure pulses to the inner ear via the oval window. The fluid pressure waves produce relative motion of hair cells in the cochlea which directly sends hearing signals via nerves to the brain.

Another device has been developed to enhance hearing in an individuals having a nearly-complete loss of hair cells within the inner ear or cochlea. Such a device is referred to as a cochlear implant. The device is invasively inserted within the helical formation of the cochlea. The implant directly electrically stimulates various regions of the cochlea to impart a sensation of hearing within the nerves of the cochlea communicating directly with the brain. However, such a hearing aid can damage the cochlea and must only be administered to patients who have lost nearly all functional acoustic hearing.

SUMMARY

Pursuant to this invention, a method for diagnosing the electromotility of hair cells within an inner ear is provided by applying an electrode proximate the round window of the inner ear so as to electrically stimulate outer hair cells within the cochlea. The electrically stimulated hair cells produce otoacoustic emissions. The otoacoustic emissions produced by the hair cells can be evaluated to determine the electromotility of hair cells in the inner ear in order to characterize the condition of hair cells within the cochlea. In order to apply current to the round window membrane, a simple wire electrode is preferably utilized externally of the cochlea to electrically evoke otoacoustic emissions. The otoacoustic emissions are the result of fluid pressure waves which act on the stapes driving the remaining middle ear bones and the tympanic membrane. The tympanic membrane, driven by the middle ear bones, acts as a speaker that produces acoustic ear canal sounds which are subsequently detected with a microphone preferably placed in the outer ear canal. Subsequently, the acoustic sounds resulting from the electrically evoked otoacoustic emissions are characterized and analyzed via signal analysis techniques.

The electric stimulus may also be used concurrently with an acoustic stimulus having a different frequency which allows for generation of distortion products. A cubic distortion product is then preferably evaluated in order to distinguish the inherent active process of the Organ of Corti. Alternatively, a two frequency electric current stimulus can be used for the same purpose. By analyzing the information on otoacoustically emitted sounds during two component electric current stimulation or electric current stimulation simultaneous with an acoustic stimulation, it is possible to assess two different quality features of the performance of the cochlea; namely, the electromotility of the hair cells within the cochlea as well as the "active process" of the organ of Corti.

The method of electric current stimulation of the cochlea can be used for a different purpose than a diagnostic test, electric current stimulation can produce a hearing aid for individuals who have a significant or complete loss of conduction in the middle ear. Patients who lack a functioning middle ear are good candidates for the resulting hearing aid. The hearing aid consists of an electrode applied adjacent the round window and configured to apply an electrical stimulation received from a hearing aid mounted outside of the ear. The hearing aid receives audible signals and converts the signals to corresponding electrical signals that are carried via one or more wires to drive at least one electrode positioned proximate the cochlea. Preferably, the electrode is positioned proximate the round window. In a case where an individual has lost middle ear conduction, the normal physiology is interrupted. Audible signals are not impedance matched and transmitted to the inner ear to form pressure waves within the inner ear fluids. By electrically stimulating outer hair cells of the cochlea from signals amplified, conditioned, and delivered as currents readily available from outer ear hearing aid, the technology can be used in this invention so as to produce pressure waves (from outer hair cell activity) within the ear that stimulate nerves along the organ of Corti and send sensations of hearing having rich information to the user's brain.

Objects, features and advantages of this invention are to provide a method of diagnosing hearing loss in an individual by determining the loss of outer hair cell motility within the cochlea, the invention provides a diagnostic device that is readily positioned within a patient's ear without actually entering the inner ear so as to prevent any complications and infections resulting therefrom. Furthermore, a hearing aid having simplified construction is presented for imparting electrical stimulation within the inner ear of patients having a general loss of middle ear function. The diagnostic test method is relatively easily implemented and the hearing aid is of relatively simple design and economical manufacture and assembly. The resulting device will remain continuously in service and have a long useful life requiring little or no maintenance.

BRIEF DESCRIPTION OF THE DRAWINGS

Preferred embodiments of the invention are described below with reference to the accompanying drawings, which are briefly described below.

FIG. 7*a* is a somewhat diagrammatic illustration of sound transmission from an ear canal through the middle and inner ear of a healthy, normal individual;

FIG. 7*b* is a somewhat diagrammatic illustration of the application of electric current to the inner ear via an electrode to produce acoustic sounds in the outer ear canal from electrically-evoked otoacoustic emissions in an inner ear canal for an ear having a normally functioning middle ear structure;

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

The cochlea, as a hydromechanical frequency analyzer, has extremely high sensitivity and a wide dynamic range. It is evident that the sensitivity and frequency selectivity of the cochlea are related to the nonlinear behavior of the basilar membrane. Gold, T. Proc. R. Soc. London Ser. B (Biol. Sci.) 135, 492–498 (1948), proposed over four decades ago that cochlear tuning and sensitivity are the result of a feedback system consisting of mechanical-to-electrical transduction process coupled to a piezoelectric-like electric-to-mechanical transduction process. Evidence for some type of nonlinear feedback system was revealed with the discovery of stimulated, spontaneous, and other otoacoustic emissions from the cochlea. Since then, the relationship between nonlinear processes in the cochlea and otoacoustic emission generation has been intensively studied. It has been shown that an otoacoustic emission occurs when alternating current is delivered into a scala media by Hubbard and Mountain, Science, 222, 510–512 (1983). It has also been found by Brownell, et al. Science, 227, 194–196 (1985) that the outer hair cells in the cochlea exhibit voltage-dependant length changes in response to electric stimulation at acoustic frequencies in vitro. These findings have made plausible the hypothesis that outer hair cells act as the electromechanical agents in a feedback system that is essential to normal auditory function. Although the study of outer hair cell motility in vitro and otoacoustic emissions in vivo provides some knowledge of the cochlear electromechanical feedback mechanism, fundamental questions remain as to the relationship between normal cochlear function and outer hair cell motility observed in vivo. A paradox is apparent, in that electromotility of outer hair cells is robust in vitro, but cochlear sensitivity and frequency tuning are extremely vulnerable to physiologically relevant manipulations such as exposure to loud sounds, ototoxic drugs, and metabolic stress.

Figure 1:
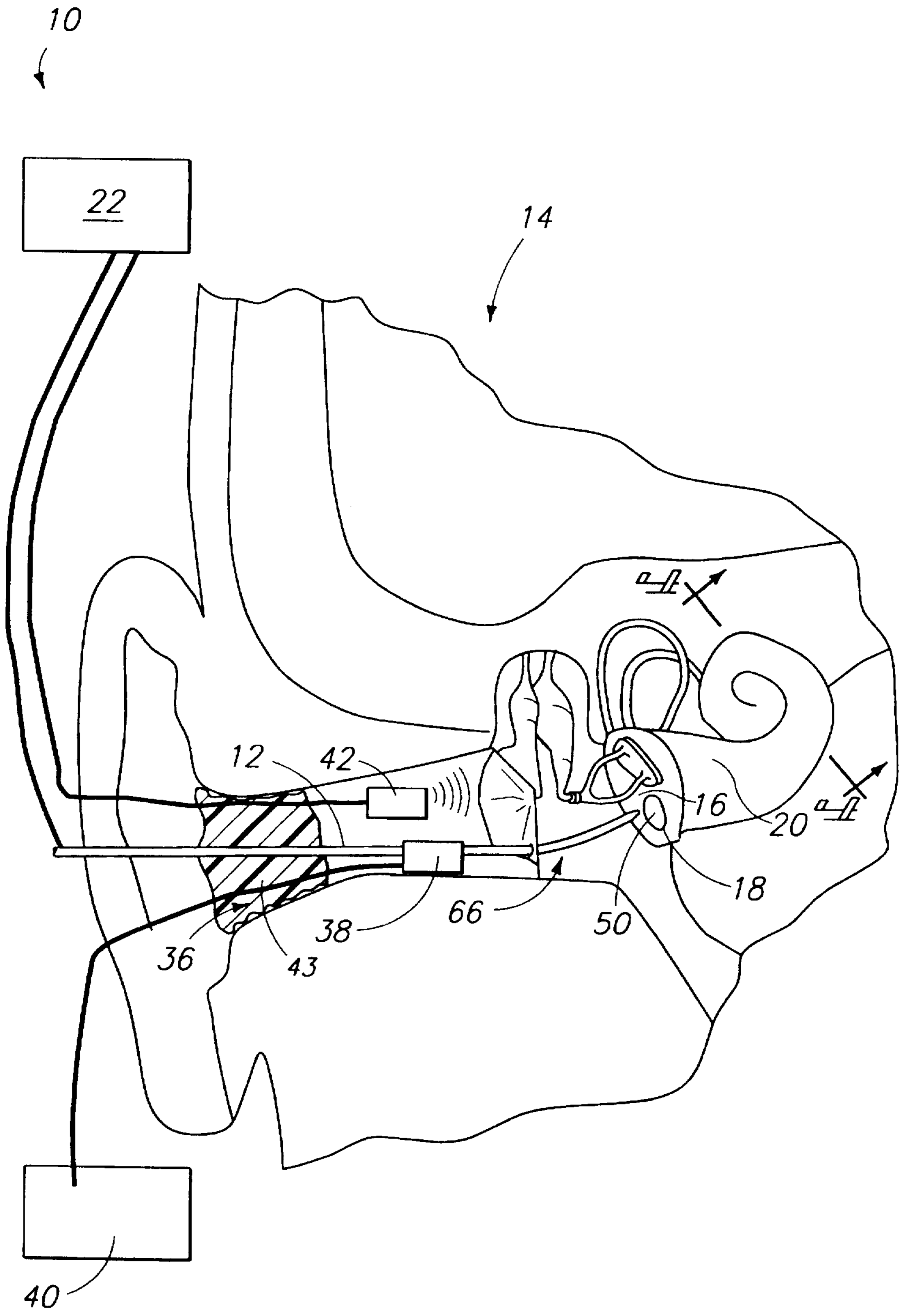
FIG. 1 is a somewhat diagrammatic sectional view of the structure of a human ear during implementation of the diagnostic methods of this invention.

FIG. 1 illustrates a diagnostic device 10 embodying this invention with a wire electrode 12 inserted within an ear 14 of a patient. The tip of electrode 12 is either placed directly on a round window, or is placed in contact with bone adjacent a round window 18 of the cochlea 20. Preferably, the electrode is placed on the round window. Alternatively, where accessibility to the round window is hindered, the electrode is placed on the bone adjacent the round window. Alternatively, the electrode can also be placed directly on the bony promontory 16. Additionally, the electrode can more readily be placed immediately adjacent the round window by bending the wire electrode to better conform and navigate through the ear canal 36. Alternatively, the wire electrode 12 can be formed from a straight needle.

The electrode 12 is inserted into the middle ear by delivering the electrode through the outer ear canal and inserting the electrode through the tympanic membrane into the middle ear. A hole can be formed by forcing an end of the electrode through the tympanic membrane. Optionally, the hole can first be formed, after which the electrode 12 is inserted through the hole. One way of first forming the hole comprises surgically forming the hole in the tympanic membrane. In all configurations, an electrical signal from a signal source 22, or electrical signal generator provides an extra-cochlear application of current to the bone either immediately adjacent the round window, or directly on the round window. The current, acting through the round window or the bony wall of the cochlea, excites hair cells within the inner ear to produce electrically-evoke otoacoustic emissions (EEOE) which emerge from within the internal structure of the fluid-filled cochlea. As a result of fluid pressure waves are produced within the cochlea at the frequency of the electric stimulus applied by the electrode 12, these fluid pressure waves further excite the remaining structure of the fluid-filled cochlea, resonating the structure of the cochlea the manner that it normally functions when receiving acoustic waves via the processes of the outer and middle ear. The electrically evoked otoacoustic emissions that emerge from the cochlea manifest themselves as corresponding acoustic sounds in the outer ear canal.

Figure 2:
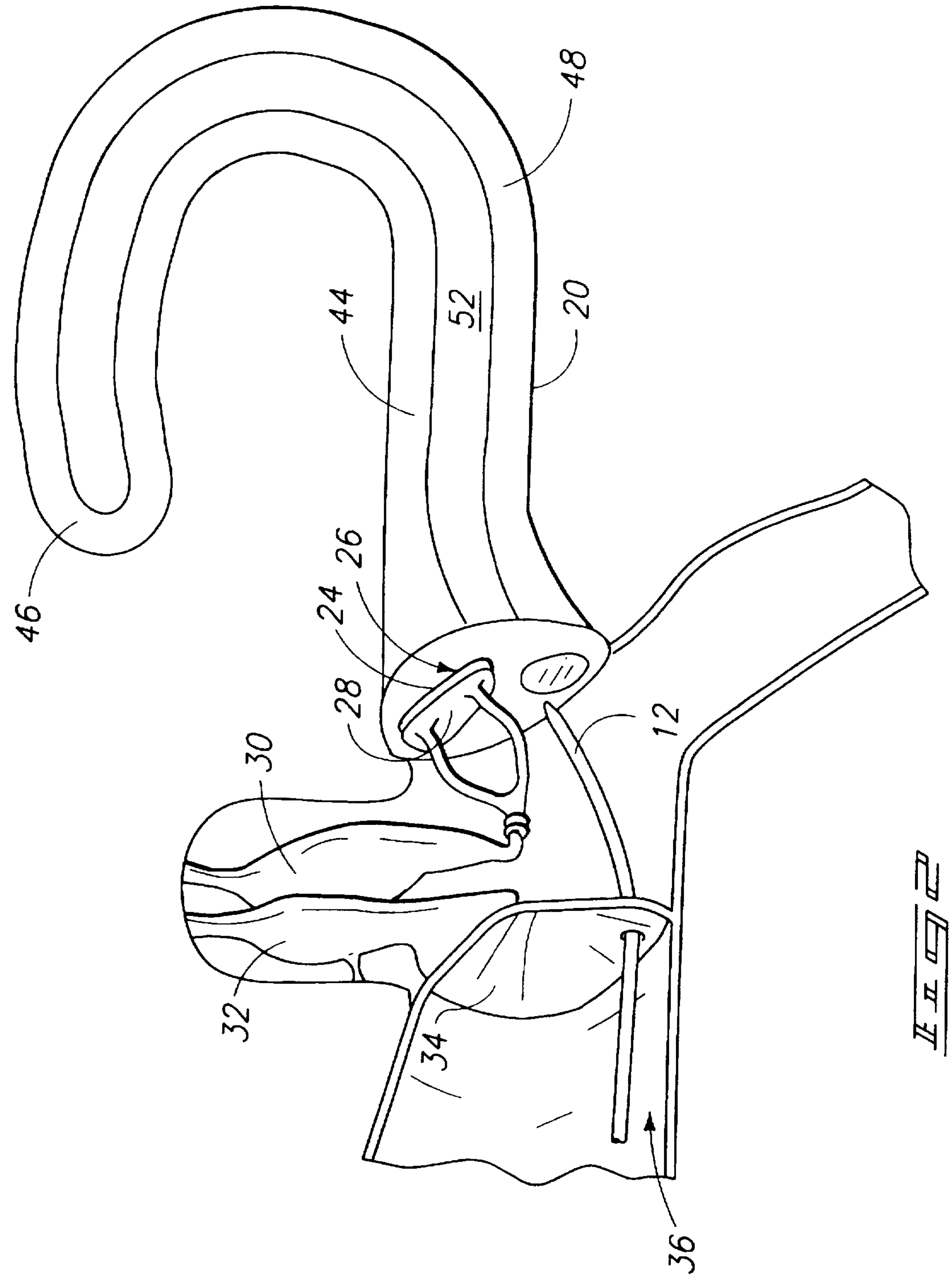
FIG. 2 is a simplified and somewhat diagrammatic enlargement particularly of the middle ear and inner ear portions of FIG. 1.

Various sites can be used to place electrode 12 in order to ensure the transmission of electric current stimulation within the cochlea 20. Preferably, the electrode is placed and held in place as close as possible to the membrane 50 of a round window 18 as illustrated in FIG. 2. Alternatively, the electrode can be placed and held in place near the round window membrane. For example, a mount could be formed wherein a needle is directly placed on the promontory 16. Furthermore, the electrode can be alternatively placed as closely as possible the fluid spaces forming the scala vestibuli 44, scala tympani 48, or scala media 52 by placing the electrode in close position relative to either fluid space. For example, a cavity or access port could be drilled into the bone surrounding the cochlea 20 in order to allow for close proximate positioning of the electrode with respect to either fluid space. Additionally, the electrode can be placed in a more remote location from the cochlea. For example, the electrode can be placed directly on the promontory, as previously discussed, or on other bony surfaces of the cochlea, or in the mucosal surface of the middle ear space, as well as possibly the skin areas of the external ear canal, or even the surface of the head around the auricle 23.

Figure 9:
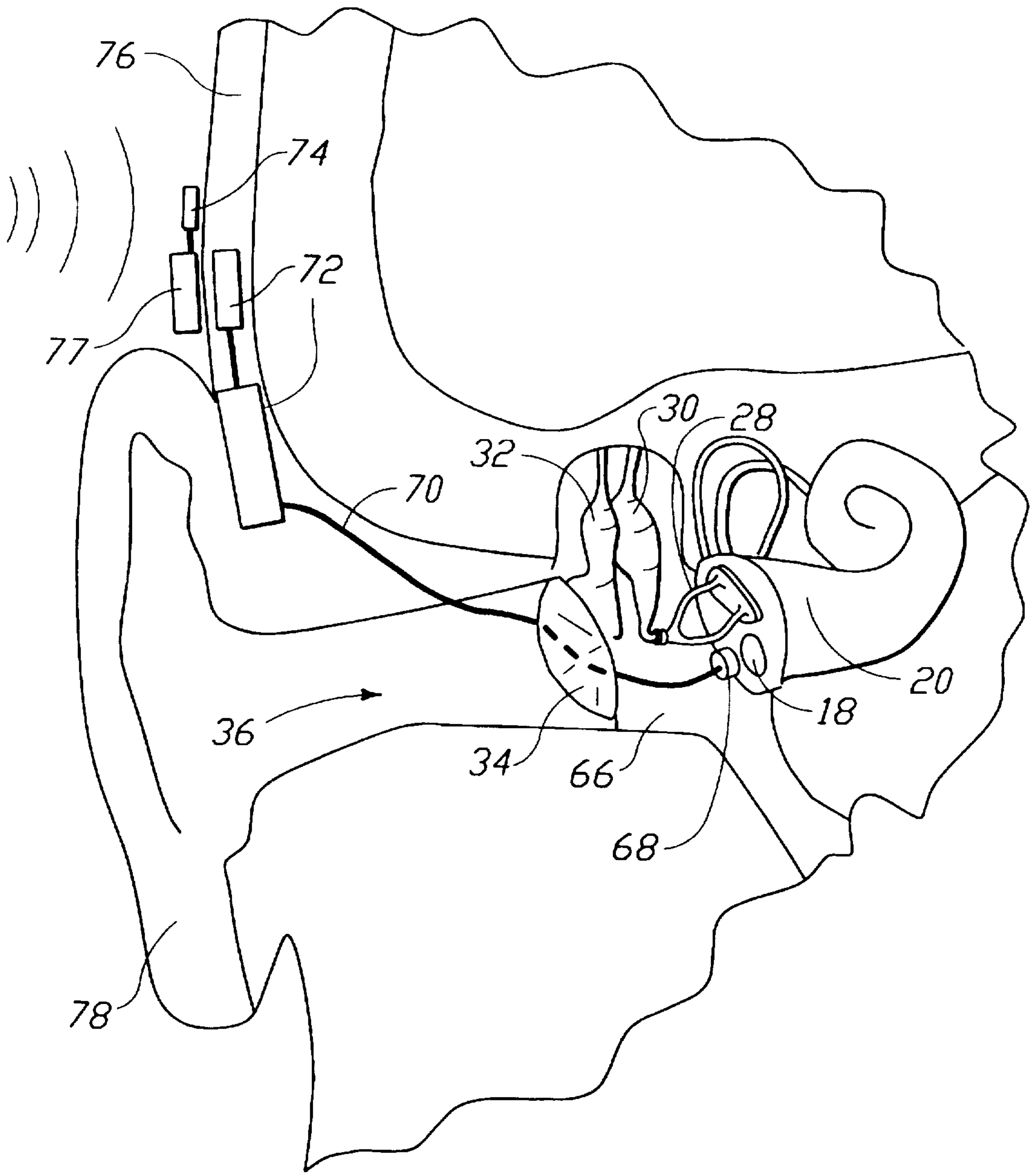
FIG. 9 is a centerline sectional view of a human ear showing a hearing aid apparatus of this invention.

For cases where it is necessary to place electrode 12 permanently in the ear 14, for example where a hearing aid is formed based upon the features of the method of this invention, the electrode can be fixed directly to the bone with a bone cement as depicted in FIG. 9. Alternatively, the electrode could be secured with a small fastener, such as a screw. Furthermore, an access port could be drilled into the bone providing a passage in close proximate position adjacent the cochlea to provide for close positioning of the electrode thereto. In such a case, the electrode could be securely packed into the passage with a snug fit, or could be cemented therein.

Figure 3:
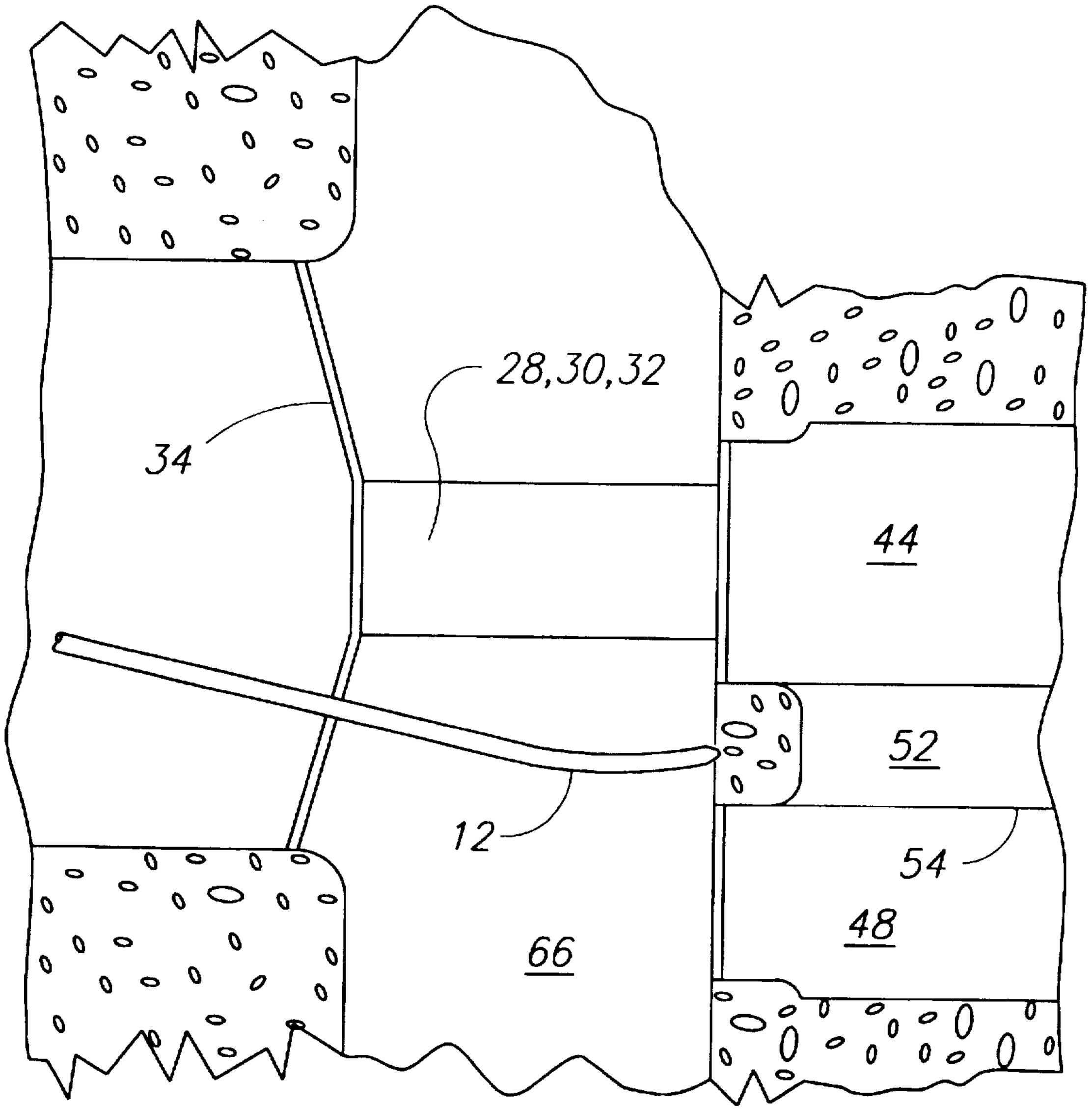
FIG. 3 is a simplified diagram depicting the physiological coaction of a simplified ear drum, middle ear, and cochlea for an individual having a healthy ear and depicting the diagnostic methods and device of this invention.

As shown in FIGS. 1 and 2, the electrically-evoked otoacoustic emissions produced within the cochlea 20 take the form of fluid pressure waves travelling within the cochlea. The waves travel in the cochlea where they finally cause motion of the basilar membrane 54 or of the stapes 28 in the oval window 26. The pressure waves produced by the resulting vibrations of hair cells in the cochlea and inner ear structure produce displacements of the stapes 28 which act on the other bones of the middle ear; namely the incus 30 and malleus 32, which together drive the tympanic membrane 34 to produce corresponding audible sounds 37 in the ear canal 36, as shown in FIG. 7-B. A simplified construction of the ear is illustrated in FIG. 3. A microphone 38 is positioned within the ear canal 36 to detect and capture any resulting acoustic sounds in the ear canal evoked from the electrically-evoked otoacoustic emissions within the cochlea. Microphone 38 then converts the sounds to electrical signals which are analyzed with the aid of one of several commercially available or custom designed signal analyzers 40. Preferably, an ear plug 43 is inserted into the ear canal 36 while detecting the acoustic sounds. A typical analysis technique is disclosed by M. L. Whitehead et al., "Measurement of Otoacoustic Emissions for Hearing Assessment", IEEE Engineering in Medicine and Biology, April/May 1994, pp. 210–226, hereinafter incorporated by reference.

Preferably, an acoustic signal generator, or speaker 42 is also placed within the ear canal 36 in order to deliver audible signals through the cochlea 20 via the normal audible conduction path of the membrane 34 and bones 28–32 in addition to the input of the electrical signal via electrode 12. Alternatively, the speaker can be placed outside of the ear canal. Preferably, more than one signal is provided to the cochlea in order to produce distortion products for signal analysis purposes that assist in characterizing the structural response in physiology of the inner ear. The applied electrical stimulus generates an acoustic emission at the same frequency of the electrical stimulus which results in intracochlear acoustic energy to drive the inner structure of the cochlea, the bones of the middle ear, and the tympanic membrane. Typically, the resulting acoustic emission is measured in the ear canal. When an acoustic stimulus 35 is given to the ear as shown in FIG. 7A, there is a reflected otoacoustic wave 37 that subsequently emerges from the ear. Although the wave is small in amplitude, it directly relates to inner ear sensitivity. Therefore, while stimulating with an acoustic signal an otoacoustic signal is produced in response. Although the resulting otoacoustic signal is weak, it is presently not used for any clinical tests because the dominant acoustic energy being supplied to the cochlea essentially masks out the otoacoustic signal. It is presently believed that this small evoked otoacoustic signal resulting from application of an audible signal to the ear is an otoacoustic signal essentially at the frequency of the primary, or audible signal input into the ear. When an electrical stimulus is used instead of an acoustic stimulus, the electrically evoked otoacoustic emission is at the same frequency as the electrical stimulus but now is no longer masked by any acoustic signal that needs to be delivered at the same frequency.

When applying an electric stimulus via the electrode 12 solely by itself, there is no acoustic signal present which might mask the produced otoacoustic signal. Therefore, the ability to capture and characterize this otoacoustic signal is significantly enhanced. In order to better study the function of internal functional features of the cochlea, the two frequency signal inputs are preferably provided to the ear in order to study resulting distortion products. To produce a distortion product, a plurality of stimuli or signals are simultaneously input to the ear in order to analyze the effects of harmonics and intermodulation components created by the structure of the inner ear, or cochlea.

Preferably, two electric stimuli, or one electric and one acoustic with the signals having distinct separate frequencies are simultaneously delivered to the ear canal 36 via speaker 42 or wire 12, wherein microphone 38 records the resulting otoacoustic emissions. The resulting primary otoacoustic emission and the distortion product is captured and measured via one of a number of suitable signal analyzers 40 where the characteristics of the inner ear can be analyzed via one of several commonly known signal analysis techniques. Preferably, the electrical signal is separately applied by electrode 12 as shown in FIG. 7B. The electrical signal provides a primary frequency stimulus which is preferably separately applied to the ear in order to detect the acoustic form of the electrically-evoked otoacoustic emissions 37 as manifest in the ear canal 36. Alternatively, a two frequency signal can be applied by the electrode 12. Alternatively, an electrical signal having two frequency components can be applied concurrently with application of acoustic stimuli. In a preferred implementation, the analysis will first consist of application of a single frequency electrical stimulus to evoke otoacoustic emissions. Hence, a two frequency test is first run with two electrical tones, and then, stimulation is applied separately via an electrical signal through electrode 12 simultaneously with an acoustic signal through speaker 42.

Alternatively, the electrical stimulus from electrode 12 could be concurrently applied with the acoustic stimuli. In one version, one electric stimuli plus one acoustic stimuli would give the desired intermodulation product. Furthermore, two electric stimuli, each having a distinct and different frequency, would produce the same result.

In accordance with invention, the direct placement of the tip of electrode 12 in abutment either with the round window 18, or the bone surrounding the round window 18 insures that alternating current is delivered by the electrode through the adjacent round window 18 into the cochlea in the form of extra cochlear current. By placing the electrode against the promontory 16 or, if possible even closer to the round window, the electrode is better able to locally apply an electrical stimulus through the round window into the hair cells of the cochlea. In the two above mentioned alternative implementations, audible sounds are concurrently applied to the external ear canal via speaker 42. By simultaneous application of at least two signals, either electric/acoustic, electric/electric, or acoustic/acoustic, a cubic (or third order) intermodulation distortion product (DP) emission and an emission at the electrical primary frequency are measured and evaluated by applicants.

In contrast, previous investigators have utilized first-order, sum and difference tones to study specific intermodulation distortion products via use of an invasive glass microelectrode for injecting current directly into the inner ear in combination with an acoustic stimulus. It has been applicant's experience that the cubic tones of the third-order intermodulation distortion product better characterize other "normal" functions of the cochlea that are not possible by measuring the first-order tones. As a result, diagnostic procedures implemented via a signal analyzer 40 are better able to determine the structural response of the cochlea and the electromotility therein in order to characterize normal cochlear function.

Figure 4:
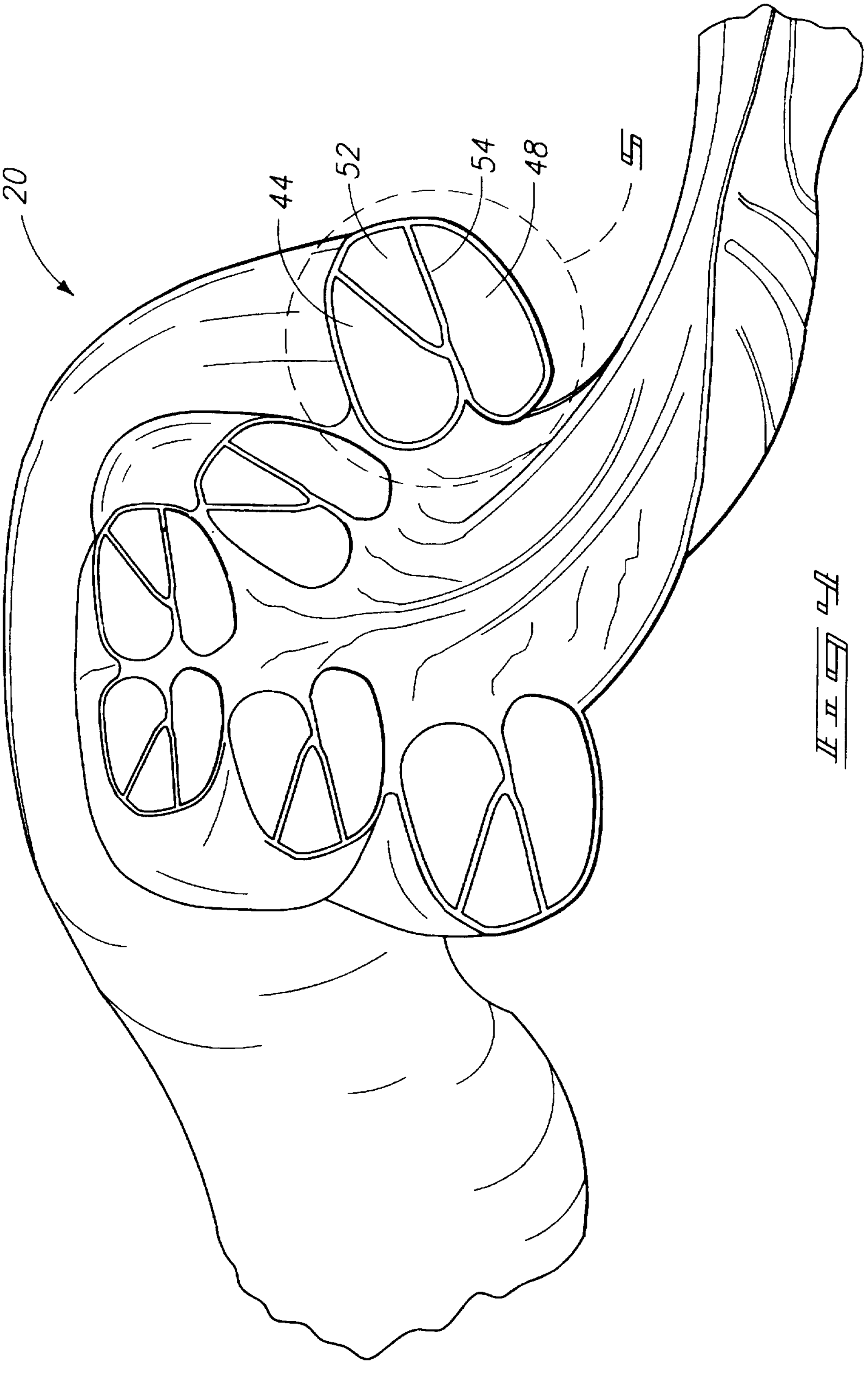
FIG. 4 is a partial sectional view taken along line 4—4 of FIG. 1 showing the helical construction of a cochlea.
Figure 5:
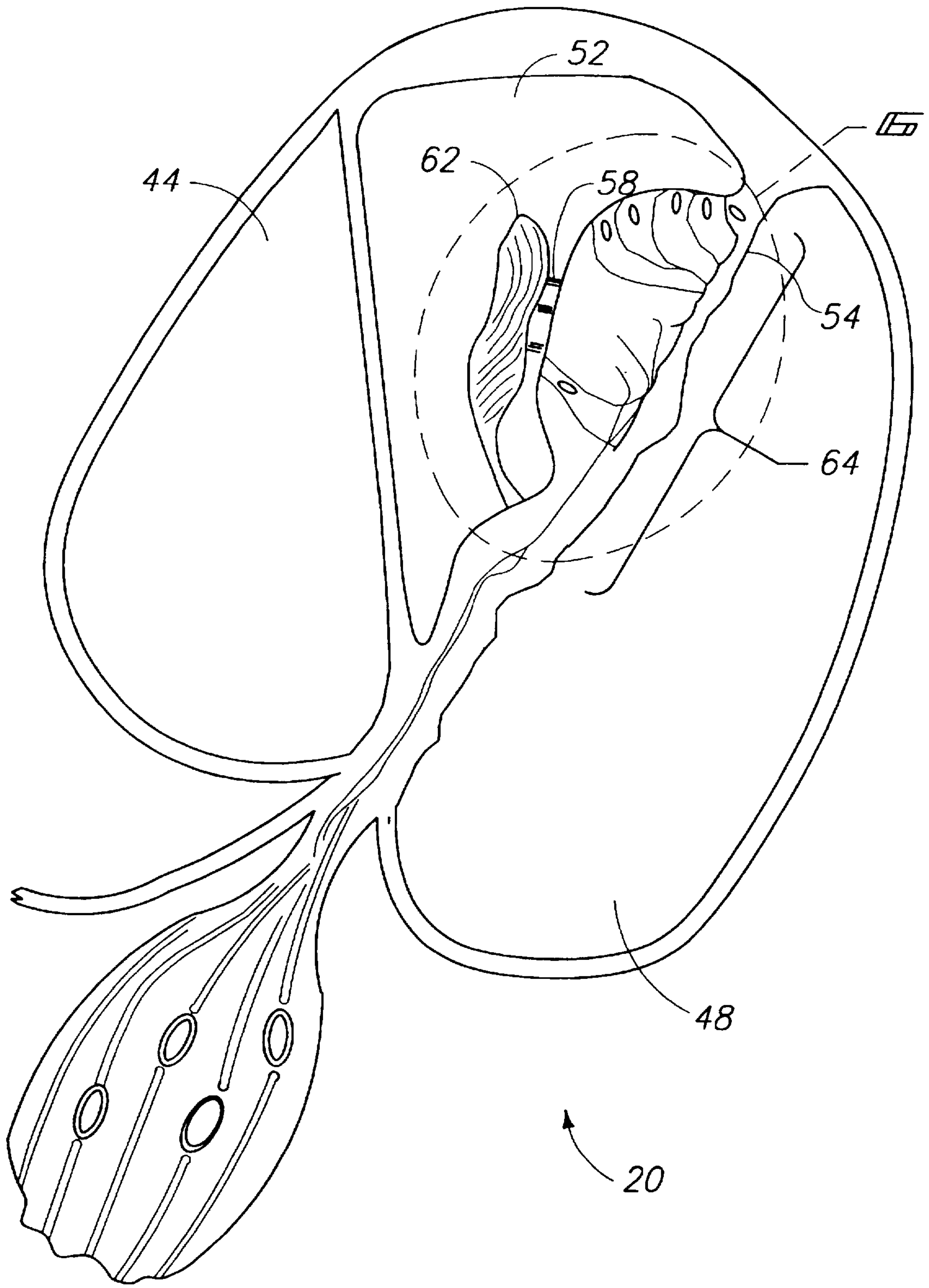
FIG. 5 is a sectional view taken along the region 5 of FIG. 4.
Figure 6:
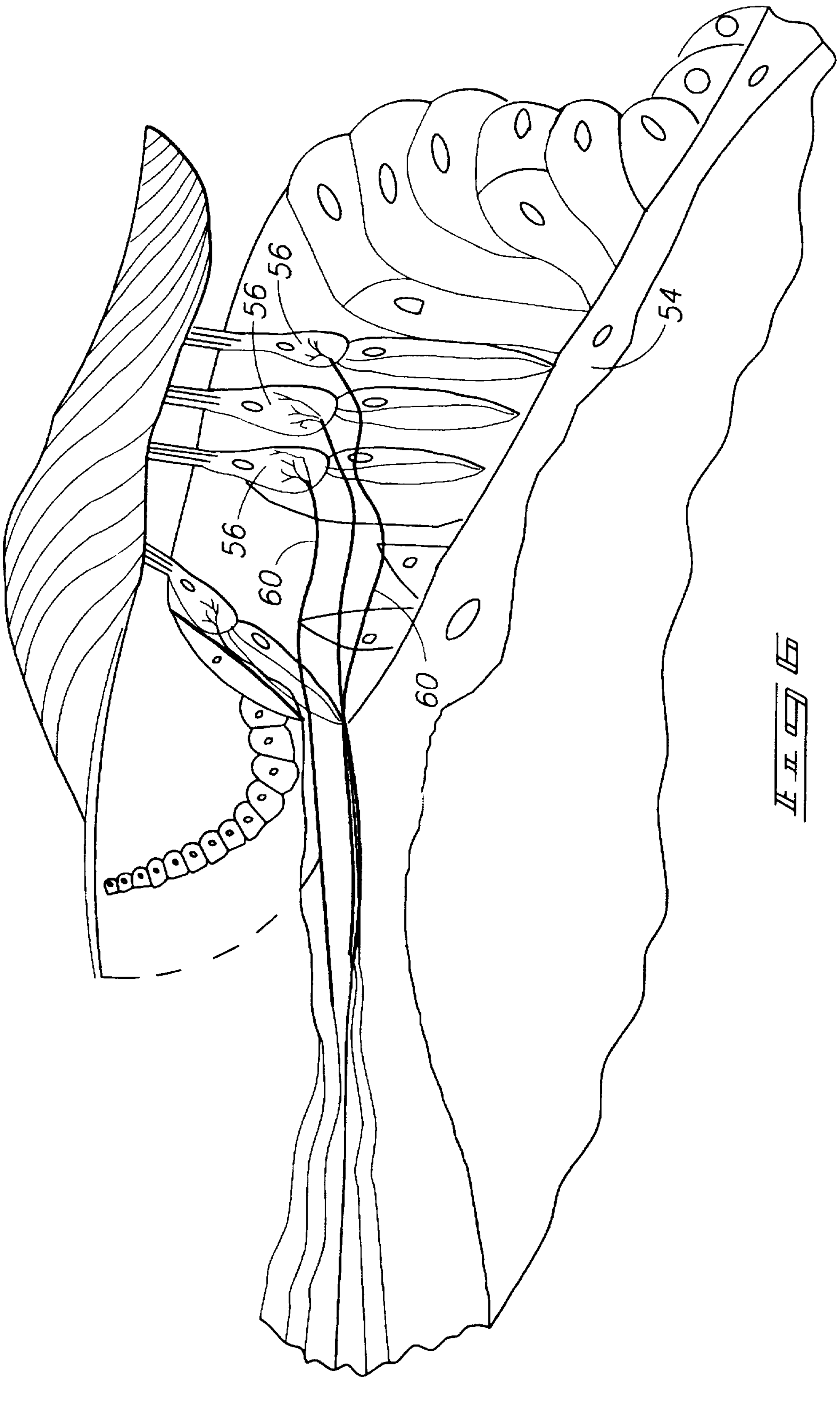
FIG. 6 is an enlarged sectional view taken generally along region 6 of FIG. 5.
Figure 8:
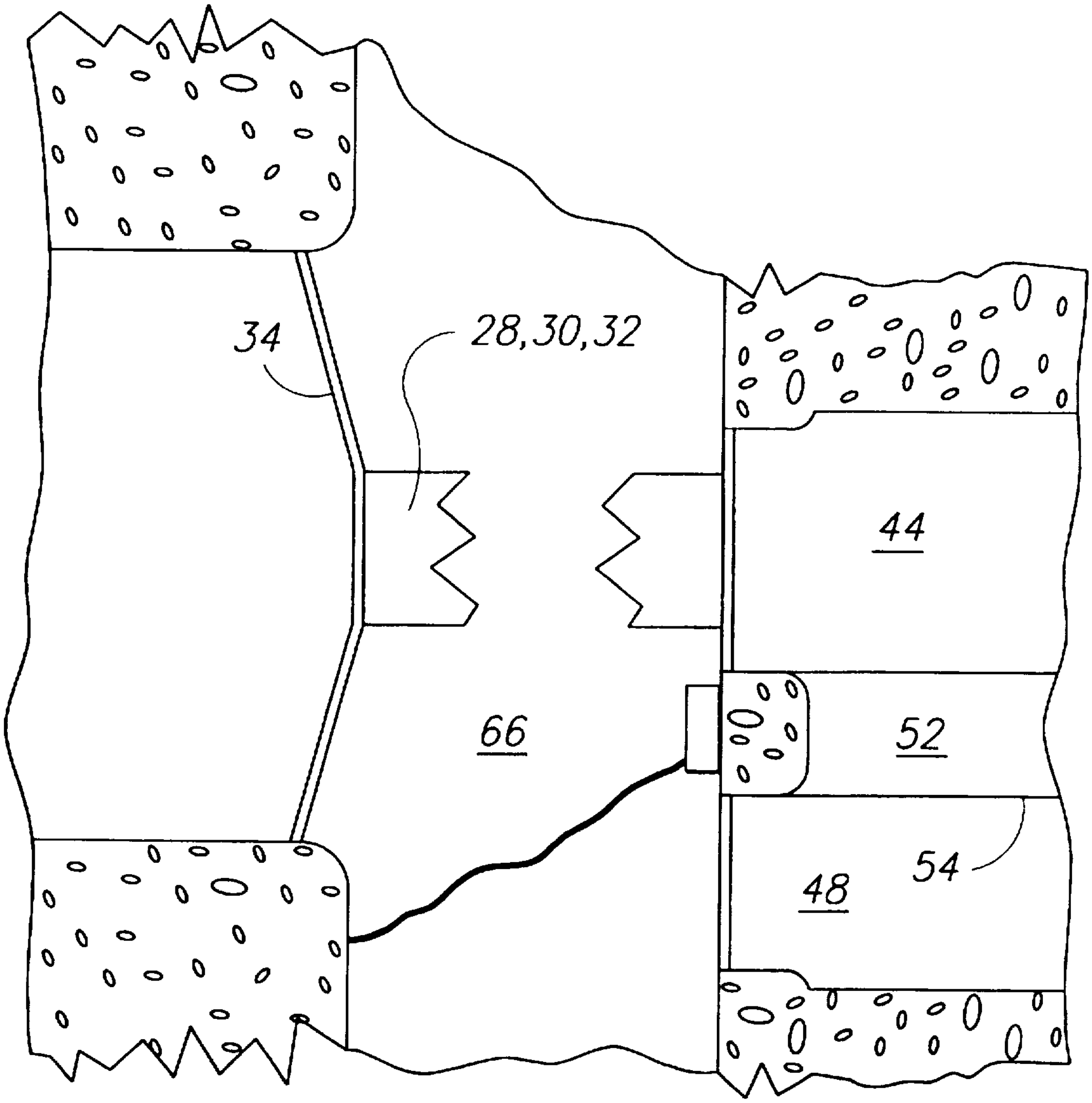
FIG. 8 is a somewhat diagrammatic view of the ear drum, middle ear and cochlea similar to that depicted in FIG. 3, but for an individual having middle ear hearing loss and incorporating a hearing aid electrode of the device of this invention.

It is desirable to evaluate the cubic distortion product in order to distinguish the inherent electromotility of the outer hair cells 56 from a secondary process which is commonly referred to as the "active process" of the organ of Corti 64 as shown in FIGS. 4–6. In order for normal hearing to occur, it is necessary to have normal outer hair cells and a normal active process, along with inner hair cells, afferent fibers, and many other components of the normal inner ear. Thus, by analyzing the information present in the otoacoustically emitted sounds during electric current stimulation, and also either simultaneously or subsequently measuring the sounds resulting form an acoustic stimulation, it becomes possible to assess the two different quality features which characterize the total performance of the cochlea; namely, the electromotility of the hair cells within the cochlea, as well as the presence of a normal active process of the Organ of Corti 64 within the structure of the cochlea proper.

FIG. 2 depicts the relationship between the ear canal 36, the middle-ear bones 28–32, and the cochlea 20. In a normal ear, stimulation of the inner ear occurs as pressure waves that impinge upon the tympanic membrane, causing small displacements of the membrane in corresponding relation to the impinging pressure waves. The tympanic membrane malleus 32, incus 30, and stapes 28 are configured to function cooperatively as a mechanical amplifier which transfers and amplifies small vibrations connected by the tympanic membrane in the form of larger vibrations acting about the stapes. The stapes 28 in combination with a circumferential ligament 24 vibrates in the oval window 26. Movement of the stapes 28 produces pressure waves inside the inner ear that travel through the fluid filled cochlea 20. More particularly, the oval window communicates directly with the scala vestibuli 44 allowing production of pressure waves therein. The distal end of the scala vestibuli terminates in a helicotrema 46 which passes in fluid flow communication to a scala tympani 48. The helicotrema acts as a pressure relief valve between adjacent portions of the inner ear, resulting effectively in a mechanical low pass filter. The walls of the scala vestibuli are substantially formed from bone and, as a result, are largely inflexible. The round-window membrane 18 displaces in response to the received pressure waves so as to accommodate pulses contained within the completely fluid-filled cochlea.

Additionally, the scala media comprises a cochlear duct formed between the scala vestibuli 44 and the scala tympani 48. During creation and propagation of the previously mentioned pressure waves within the cochlea, most of the pressure is actually transmitted from the scala vestibuli 44 into the adjacent cochlear duct of scala media 52. As a consequence, a basilar membrane 54 formed within the duct is caused to vibrate in response to the propagating pressure waves within the cochlea.

As best shown in FIGS. 4–6, pressure waves propagate within the helically shaped cochlea 20 in a forward direction along the scala vestibuli 44 and scala tympani 48. In this manner, each pressure wave passes by a particular region of the basilar membrane in a forward direction. With each pressure change that occurs within the inner ear, a propagating vibration wave travels along the basilar membrane to produce displacements at structural locations along the membrane that resonant when subjected to the corresponding frequency of vibration. Hence, the portions of the membrane displaced by a wave varies with the frequency of the wave produced by a sound source traveling therealong. It goes without saying that a sound source having a multitude of different frequency components will excite various corresponding regions of the basilar membrane into a vibrating resonating structural response.

From a mechanical point of view, the basilar membrane is a tuned structure having specific regions that vibrate in response to application of propagating pressure waves with specific excitation frequency components. The basilar membrane carries hair cells 56 that communicate through stereocilia 58 with a tectorial membrane 62. The hair cells 56 form sensory cells for hearing, namely the inner and outer hair cells of the cochlea. The stereocilia 58 protrude from the apical surface of each of these cells to form a bundle of hairs. Each of these hairs, or stereocilium consists primarily of actin which forms a stiff rod like structure. Pressure waves produced by sound waves collected in the inner ear get passed from the ear drum to the inner ear via the bones of the middle ear causing vibration of the basilar membrane which results in angular displacement of the stereocilia 58. Angular displacement of the stereocilia results in the opening of ion channels in the cell membrane at the apical surface, or tip. Opening of the ion channels results in a flow of ions, and subsequently a change in voltage drop across the membrane of the hair cell 56 in response to the pressure wave produced by the sound wave. Therefore, a receptor potential is formed by the resulting voltage drop which leads to synaptic transmitter release at the basilar end of the cell. The synaptic transmitter release pursuant to standard neurophysiology, triggers action potentials and internal impulses to the brain that comprise the individuals ability to perceive sound. Therefore, the movement-induced voltage production of the stereocilia within the inner ear of the cochlea provides the driving force which triggers our hearing processes.

Consequently, pressure waves produced by a sound wave collected in the ear canal having one or more frequency components travels through the cochlea to excite a portion of the basilar membrane that is structurally tuned to vibrate when subjected that specific frequency. Vibration of the basilar membrane moves the hair cells in relation to the tectorial membrane as shown in FIG. 6. As a result, the stereocilia which are affixed to the tectorial membrane trigger stresses in the hair cells which sends signals down nerve fibers 60 to the human brain. As a consequence, an individual hears a corresponding frequency-based signal component first collected as an audible signal within the ear canal 36.

As shown in FIGS. 5 and 6, the basilar membrane 54 has regions of maximum displacement which vary with the frequency of the sound source traveling through the cochlea. The portion of the basilar membrane nearest the middle ear 66 is configured to vibrate in response to high-frequency tones. Furthermore, high-frequency sounds have a tendency to die out quickly. Therefore, hair cells carried on the basilar membrane nearest the middle ear are typically stimulated in response to high-pitch tones, as compared with hair cells in regions further displaced from the middle ear.

With decreasing frequencies of the sound wave, vibration waves must travel further down the cochlea before exciting a portion of the basilar membrane in response to progressively lower tones. Therefore, individual hair cells configured along the basilar membrane have a maximum receptor potential for a particular frequency of stimulation. Hence, frequencies incoming along a traveling sound wave within the cochlea are effectively sorted out along various regions of the basilar membrane with particular hair cells responding maximally to specific frequencies of stimulation. Generally, the outer hair cells of the cochlea closest to the round window are excited by the higher frequencies.

FIG. 7*b* illustrates a simplified representation of the application of electric stimuli with electrode 12 adjacent to the bony promontory 16 near the round window 18. The electric signal from the electrode 12 excites outer hair cells 56 in the cochlea causing a change in their membrane potential and producing electromotility. The electromotility of the outer hair cells is presently thought to actively control the micromechanical properties of the sensory or displacement response of the organ of Corti 64.

Pursuant to this invention, a hearing aid is disclosed which utilizes the features presented in FIGS. 1–8. Namely, a small electrode 68 is affixed to bone adjacent the round window 18 in order to impart electric current to a cochlea 20 to produce sensations of hearing in an individual having middle ear hearing loss. One example of middle ear hearing loss would result from arthritic conditions present at the joints formed between the stapes 28, incus 30 and malleus 32. Such a device is depicted in FIG. 9 wherein electrode 68 is preferably glued to the bone adjacent the round window 18 and a wire 70 is permanently mounted to the electrode where it extends through the middle ear 66 around an outer edge of the tympanic membrane 34 where it enters the outer ear canal 36. Preferably, wire 70 is surgically embedded in soft tissue 76 formed beneath and behind the pinna 78 of the ear. Preferably, wire 70 delivers an electric stimulus from a receiver system 72 also mounted within the soft tissue 76. Preferably, the receiver system 72 is formed from an electromagnetic coil, and includes an electromagnetically driven power circuit. Alternatively, the signals can pass through the skin with a percutaneous plug. Additionally, microphone 74 and a transmitter/receiver processor 77 are mounted behind the subject's ear under the outer skin.

The microphone 74, the hearing aid processor 77, and the receiver system 72 are presently commercially available wherein the microphone picks up audible sounds outside of the skin and behind the subject's ear such that corresponding signals are delivered to the hearing aid via processor 77. In operation, processor 77 has a battery used to create an electromagnetic signal utilized by receiver 72 to create power. Additionally, processor 77 sends a signal to the receiver 72 where it is amplified and delivered to the user's cochlea via wire 70. In this case, hearing aid 72 delivers an electric signal having one or more frequencies to electrode 68 such that the electrode delivers electric current into the cochlea which stimulates hair cells within the cochlea, which stimulates the inner structure of the ear and produces hearing sensations via the mechanisms discussed in FIGS. 1–8 in the subject's brain.

Alternatively, electrode 68 can be screwed into the bone surrounding the cochlea in one or more locations. Furthermore, a small recess or hole can be formed in bone surrounding the cochlea which allows for closer placement of the electrode adjacent to the outer tissue surfaces of the cochlea encased within the bone.

Presently, the displacement response of the organ of Corti 64 comprising traveling waves forming on the basilar membrane 54 results from intracochlear acoustic pressure produced by the electrical current-induced movements of the outer hair cells due to electromotility as shown in FIG. 7B.

In order to understand how the electromotility of the outer hair cells contributes to normal cochlear responses, in vivo tests have been undertaken by applicants to develop a novel animal model for studying the electromotility in the intact cochlea to be discussed hereinafter. Application of the alternating current to the outer hair cells by the electrode through the round window of the cochlea produces electrically-evoked otoacoustic emissions or sound at the frequency of the electric stimulus within the cochlea. As a consequence, the electrically-evoked intracochlear acoustic pressure further excite inner hair cells within the ear and produce corresponding basilar membrane motions. As a consequence, the stapes 28 in the oval window 26 moves in correspondence with fluid pressure pulses originating resulting within the cochlea. As a result, the middle ear bones 28-30 act on the tympanic membrane 34 to produce sound in the ear canal 36. In effect, motion of the stapes 24, including bones 28-32, and membrane 34 act as a sound generator driven by fluid pressure pulses within the cochlea resulting from electrically-evoked outer hair cell electromotility. Preferably, a two frequency component stimulus is subsequently presented to the inner ear in order to generate distortion, preferably third order intermodulation distortion products which are subsequently evaluated to determine the condition of the "active process" of the organ of Corti 64 as will be further discussed hereinafter.

The cubic intermodulation distortion product comprises emissions resulting from the combination of an electric stimulus applied approximate the round window and acoustic stimulus applied within the ear canal 36 to the tympanic membrane 34. As a result of recent animal studies performed by applicants, it is presently believed that emission from the cochlea at frequencies of the electric stimuli are generated by outer hair cell electromotility. The cubic intermodulation distortion product emissions characterize normal cochlear function and can be altered independently of the electromotility. Applicants have produced results which show that electromotility can be studied in vivo and that it is necessary for, but not the sole determinative of normal cochlear sensitivity. The electrically evoked otoacoustic emissions are sensed and are subsequently evaluated in order to assess the measurement of electromotility of the cochlea membrane potential. The cubic intermodulation distortion product, a second emission resulting from application simultaneously of the acoustic and electric stimuli, is used to measure normal cochlear function.

Clinical Animal Studies Verifying Otoacoustic Emissions

In an effort to confirm the production of electrically-evoked otoacoustic emissions (EEOE) as well as electrically evoked cubic intermodulation distortion product emissions, animal studies where performed by applicants on the gerbil cochlea. The above two forms of otoacoustic emissions were used in an effort to measure the electromotility and the normal cochlea function, respectively. First, tests were conducted to show the principle relationships of the EEOE measured in the ear canal to the parameters of the electric stimulus. Second, the use of acoustic and electric stimulation to produce the cubic distortion product was implemented and the relationship of the EEOE to intercochlear traveling waves was established. Thirdly, applicant's observed changes in the emissions during and after biochemical manipulations, or following death of a subject animal. The biochemical manipulations target separate mechanisms and help separate the outer hair cells electromotility as one component in a nonlinear feedback system. Furosemide was used to decrease the endocochlear potential and sodium salicylate specifically to block outer hair cell electromotility. Paraformaldehyde abolished all biologically relevant intracochlear responses.

Figure 10:
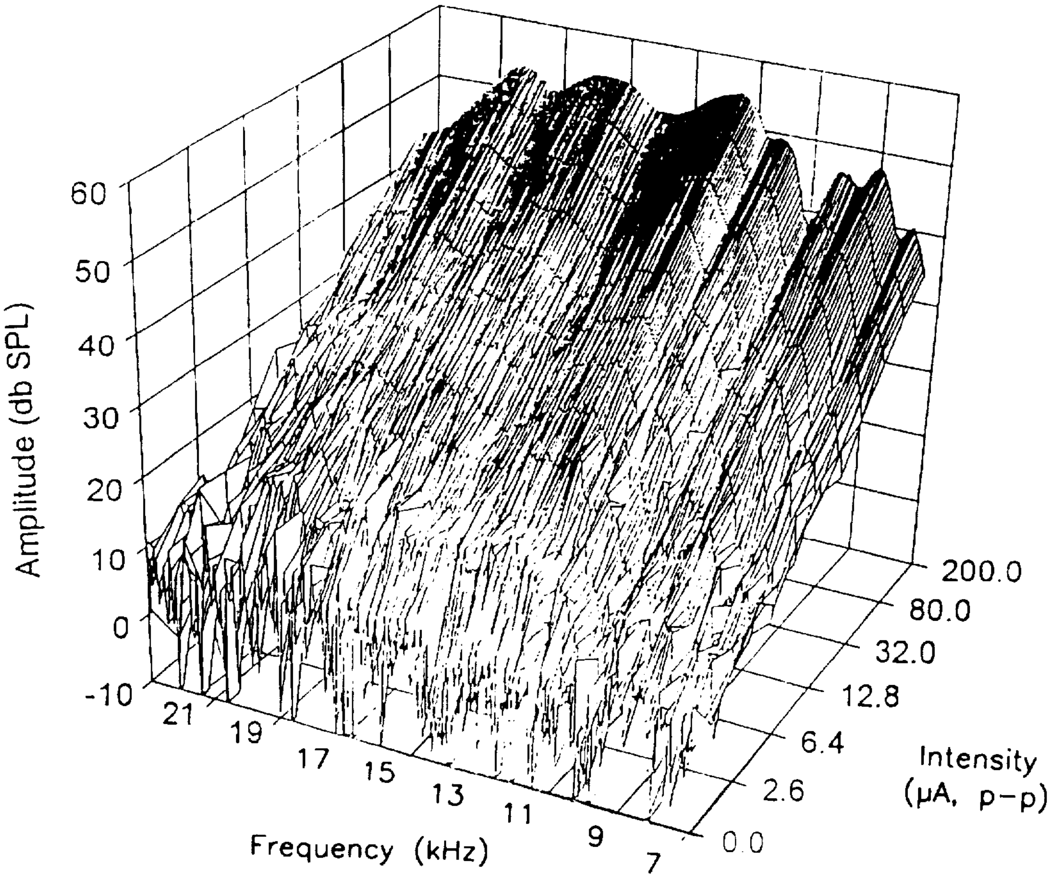
FIG. 10 is a three dimensional plot of the magnitude of a typical EEOE response.
Figure 11:
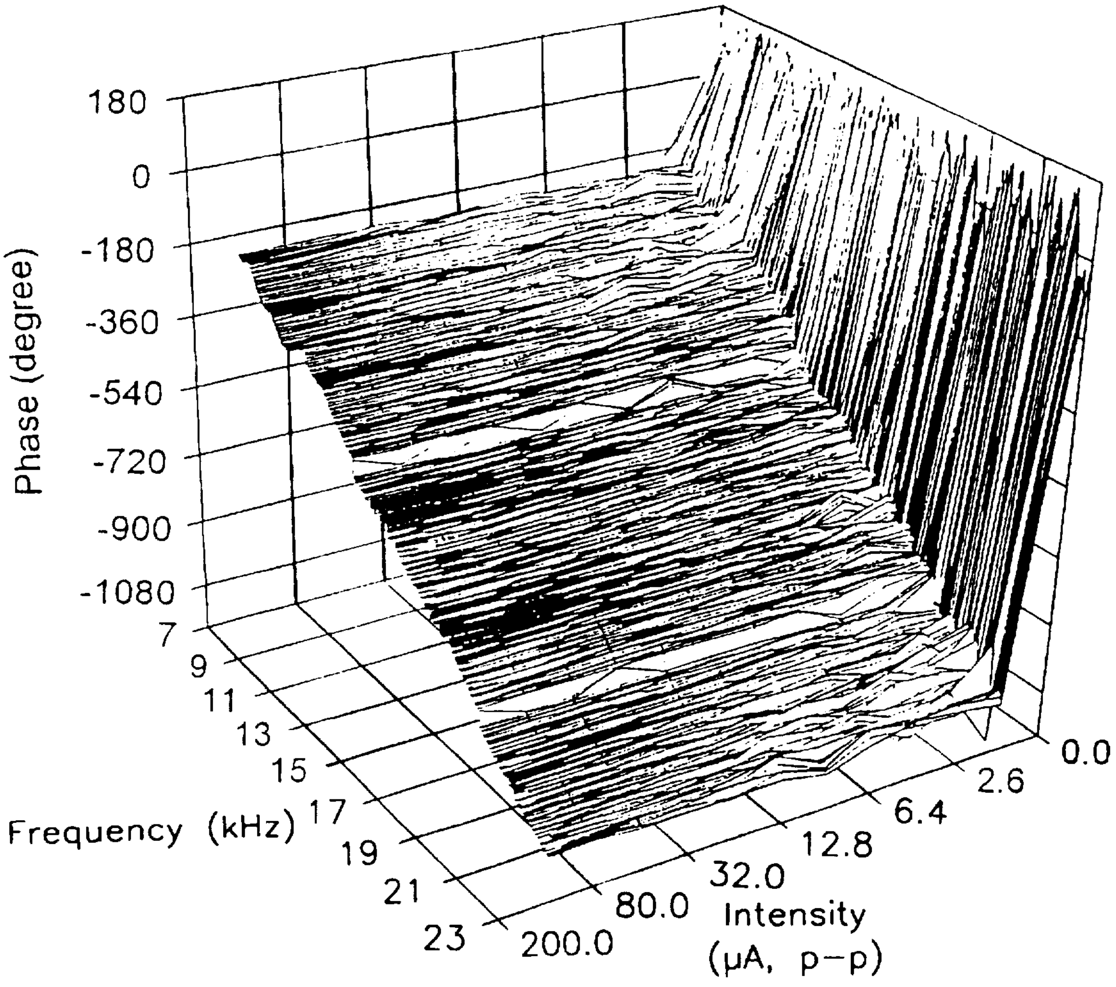
FIG. 11 is the phase of the typical EEOE response corresponding to the magnitude of the transfer function depicted in FIG. 10.

As a result of the experimental tests, the magnitude and phase of a typical EEOE response are shown in FIGS. 10 and 11. For a given intensity, the magnitude of the EEOE has a generally bandpass appearance, wherein the bandpass frequency range of the EEOE is influenced by the electrode location. For the data of FIGS. 10 and 11, the electrode was placed on the round window, near the basilar end of the organ of Corti. With the electrode more apically located, but still in the round window area, the EEOE frequency range was found to shift toward lower frequencies. The low frequency cutoff for round window stimulation was found to be in the range of 4–9 kHz. The high frequency cutoff, which shows a sharper decline than the low frequency cutoff, was located between 18–26 kHz. Across the EEOE frequency range in question, amplitude (in dB) is found to be a positive linear function of the logarithm of current intensity. The EEOE sound pressure, in other words, is a linear function of current level. As a result, applicants have concluded that an intracochlear force (i.e., sound pressure) generated by the alternating current delivered through the round window electrode has a linear relationship with current level. Only at high current levels could harmonic distortion be seen in EEOE and the level of current producing distortion was frequency-dependent (not shown).

Furthermore, notches were found in the transfer function with different depths and frequency separations existing in the transfer function (FIG. 10). Although the origin of the notches is not known at this time, they could be due, in part, to an uneven middle ear transfer function or to internal cochlear traveling wave reflections. Although applicants do not presently completely understand their function, they may be related to irregularities in the auditory threshold curve and in the otacoustic emissions that have been reported by other investigators.

The phase of the primary EEOE is a decreasing function of electrical current frequency as shown in FIG. 11. The phase has a linear relationship with frequency and shows no change with current intensity, except at the low current levels in the low and high frequency areas. Such a linear phase means that a pure time delay of approximately 200 μs dominates the response. This delay is consistent with a delay one would expect due to the propagation of the sound pressure from intracochlear generators to the microphone. The phase data indicate that sound pressure in the ear canal is dominated by waves that start to propagate from their sources (e.g., from OHCs) at the same relative phase. It is possible that the nonlinear phase of a BM traveling wave is present but its time delay is too short to be readily observed. Additionally, amplitude and phase of the zero current EEOE is included in FIG. 11 to show the frequency independence of the microphone signal, indicating a non-acoustic residual signal.

Figure 12:
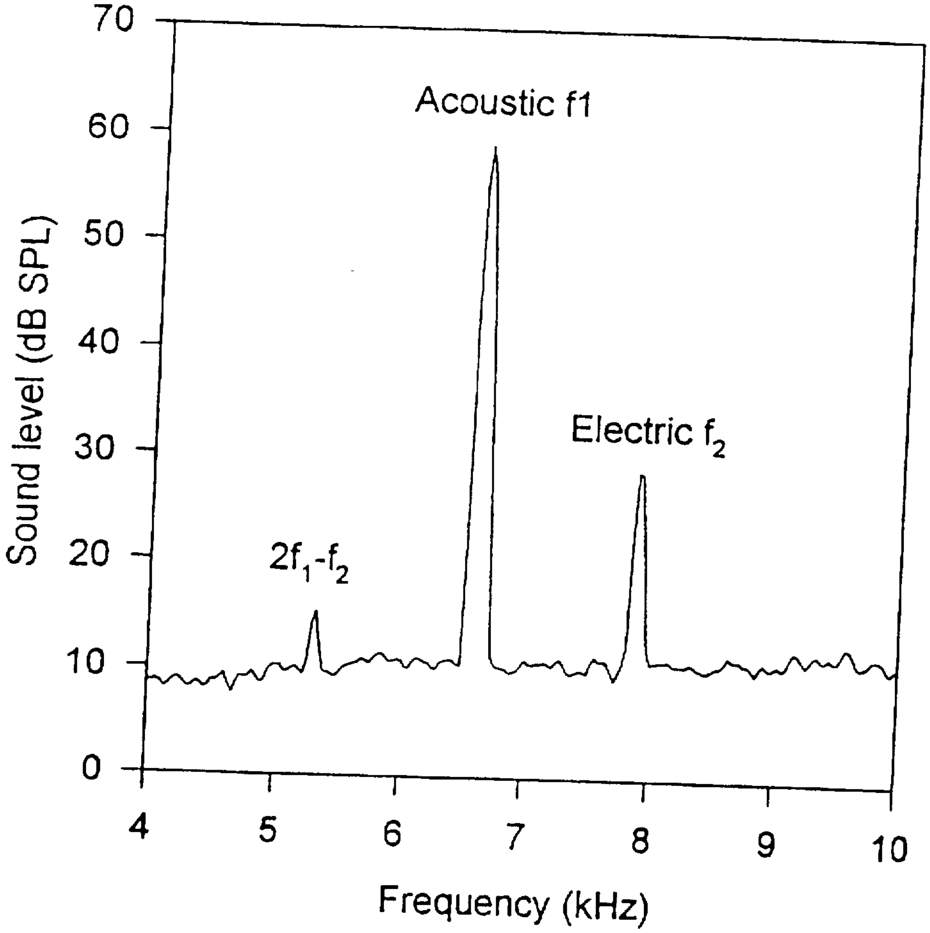
FIG. 12 depicts the distortion product provoked by an electric and acoustic stimulus.
Figure 13:
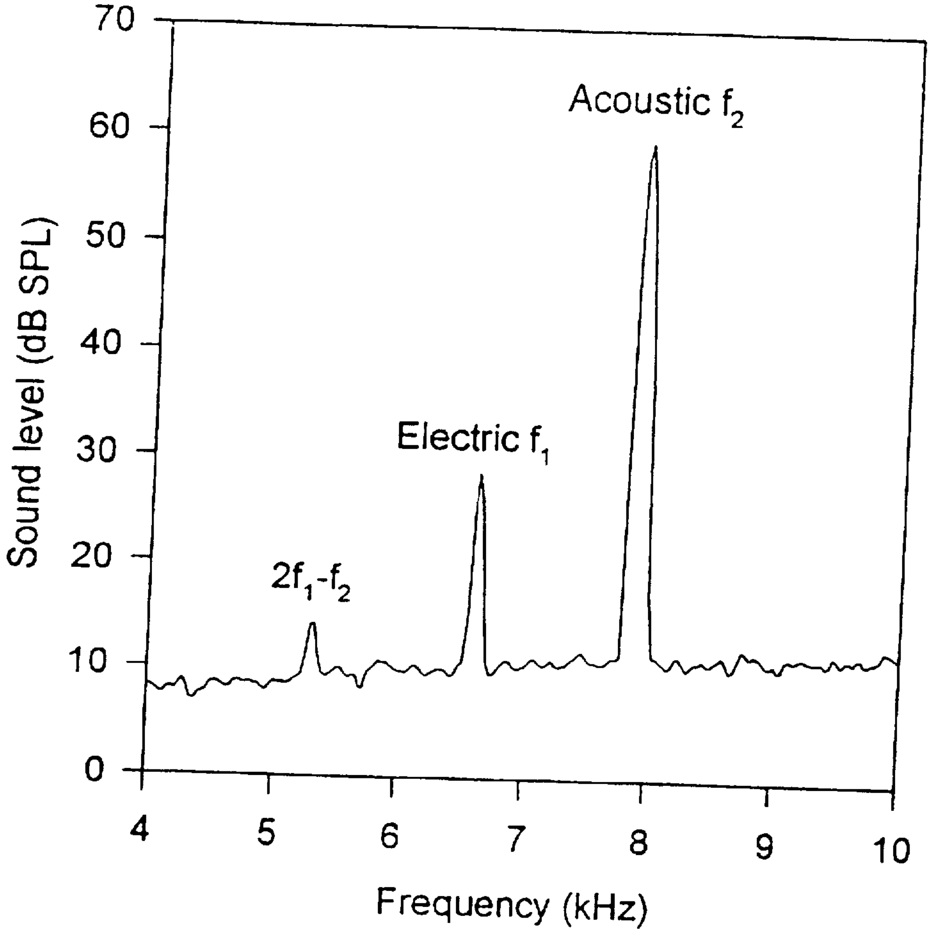
FIG. 13 depicts a distortion product produced by an acoustic stimulus where the corresponding frequencies of each stimuli were reversed for those utilized in FIG. 12.

In FIGS. 12 and 13, an otoacoustic cubic DP was provoked by an electrical current applied to the round window, combined with an acoustic tone given to the ear canal. Cubic DP is a reliable indicator of the physiological cochlear mechanism that produces the high sensitivity and narrow frequency tuning. In FIG. 12, a 60 dB SPL continuous tone at 6.66 kHz (f1) with a 400 μA (p-p) alternating current at frequency of 8.00 kHz (f2) generates a 15 dB SLP cubic DP (2f1–f2) at 5.32 kHz. In FIG. 13, an approximately equal intensity cubic DP of the same frequency was generated by reversing the frequency of the electrical and acoustic stimuli (i.e., electrical f1 and acoustic f2). No significant enhancement of the electric primary was caused by the acoustic primary tone, as has already been observed in similar experiments by others. Since in the normal cochlea the cubic DP results from the combination of two traveling waves along the basilar membrane, the data of FIG. 12 and FIG. 13 provide indirect evidence that alternating current delivered through the round window electrode provoked the same traveling wave as an acoustic stimulus at the same frequency.

Figure 14:
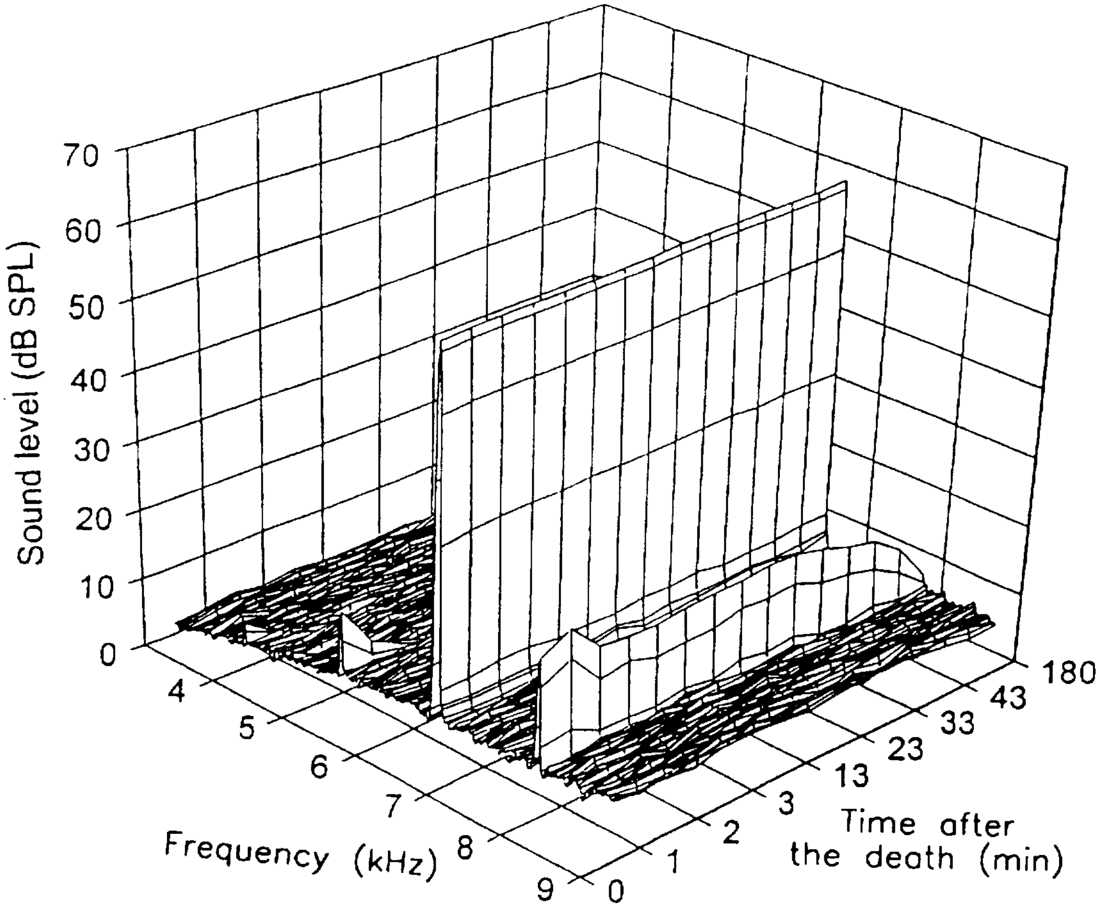
FIG. 14 depicts the change in electrically evoked otacoustic emissions and the cubic distortion product post mortem.

The change in the EEOE and cubic DP post mortem is presented in FIG. 14. The animal was euthanized by cardiac injection, which resulted in an immediate decrease in cubic DP, reaching the noise floor in less than 1 min. However, the EEOE showed a transient increase of a few dB, indicated by the data point at 30 sec after death, before decreasing to a few dB lower than original level. The EEOE decreased significantly but still had a residual value above the noise floor. The data clearly show that the cubic DP is highly sensitive to the metabolic disturbance following death, while the EEOE is resistant to this change.

Figure 15:
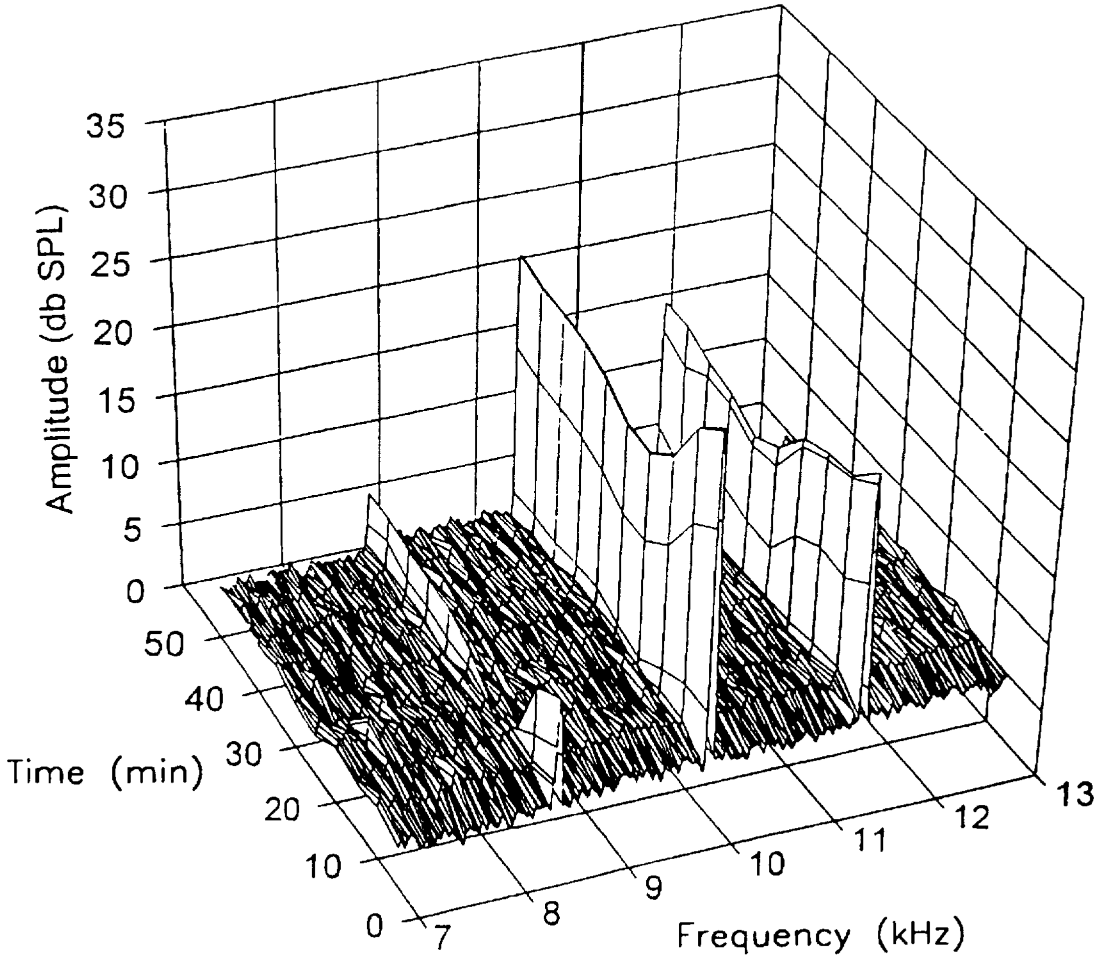
FIG. 15 depicts the effects of intravenous infusion of furosemide injected in order to identify the contribution of endocochlear potential to the electrically evoked otacoustic emissions in the cubic distortion product.

In order to identify the contribution of the endocochlear potential (EP) to the EEOEs and the cubic DP, the effect of an intravenous infusion of furosemide was observed (FIG. 15). During the 10 min drug infusion, the cubic DP decreased to the noise floor. After drug infusion, the DP gradually recovered. An EEOE at the stimulus frequency (f1) started to decrease during the perfusion and reached the minimum (about a 10 dB decrease) at 5 min following perfusion, followed by a gradual full recovery. The EEOE at the stimulus frequency (f2) showed a smaller decrease with a longer delay than f1. Neither the f1 nor the f2 EEOE showed any consistent enhanced response throughout the observation time, as has already been reported by others. The different response pattern of f1 and f2 primary EEOEs may be related to a topographic dependence of cochlear mechanical changes. The data indicate that the decrease in the cubic DP strongly depends on the furosemide-induced reduction in EP, as can be expected from the dependence of cochlear sensitivity on the EP. EEOEs are more weakly EP-dependent, which may be related to the changes of voltage-dependent OHC motility. Reduction of the EP would affect the hair cell resting membrane potential because it would change the standing current passing through the transduction channels.

Figure 16:
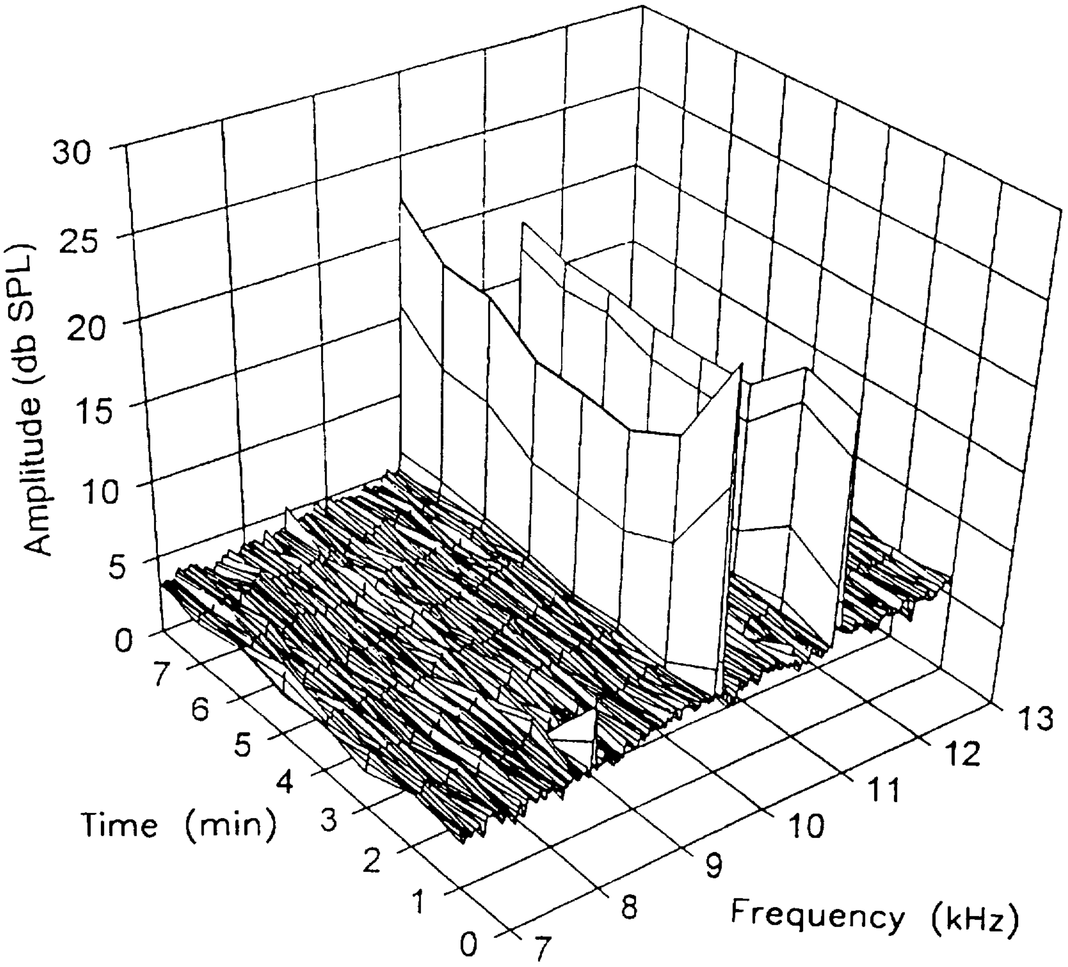
FIG. 16 depicts the effects of intra cochlear infusion of sodium salicylate to assess the relationship between the electrically evoked otacoustic emissions and the cubic distortion product.

In order to understand the relationship between the EEOEs and the cubic DP, the effects of intracochlear infusion of sodium salicylate were measured. Sodium salicylate has been shown to block OHC motility in vitro and to suppress reverse transduction in situ. As shown in FIG. 16, a 1 min infusion of sodium salicylate in artificial perilymph resulted in an immediate disappearance and only partial recovery of the cubic DP. The EEOE at the electrical frequency f1 showed a transient decrease of approximately 10 dB, followed by a full recovery. The EEOE at electrical frequency f2 increased slightly during the infusion and then showed a smaller transient decrease than f1. A 5 min sodium salicylate perfusion (data not presented) showed an irreversible decrease in EEOEs and their cubic DP. These results indicate that sodium salicylate can suppress the EEOE's and eliminate their cubic DP, as expected from in vitro studies of OHC motility. The probable mechanism is that sodium salicylate decreases OHC motility in vivo.

Figure 17:
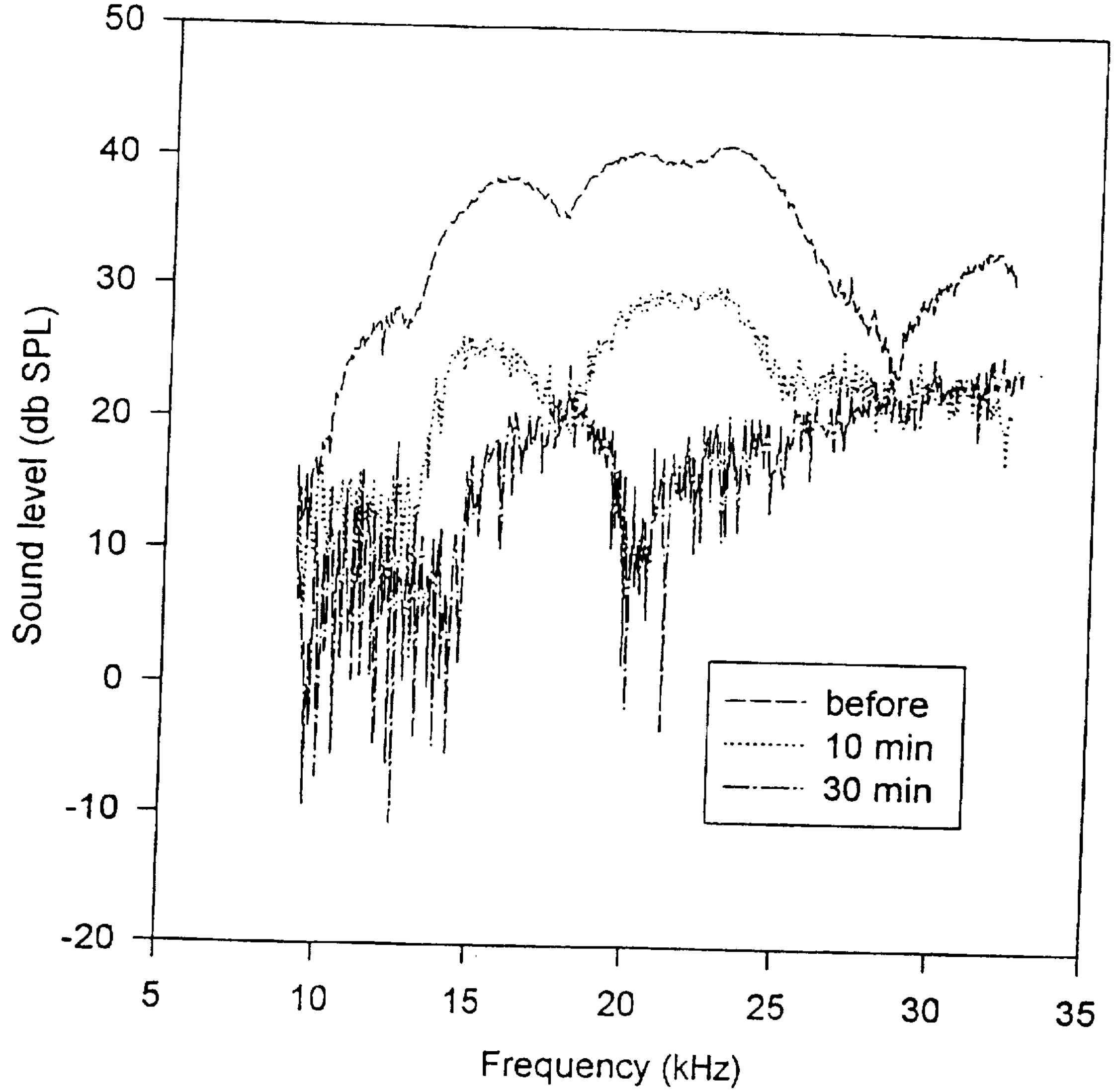
FIG. 17 is a frequency response resulting from an intracochlear infusion of 4% paraformaldehyde in order to completely block the electrically evoked otacoustic emissions.
Figure 18:
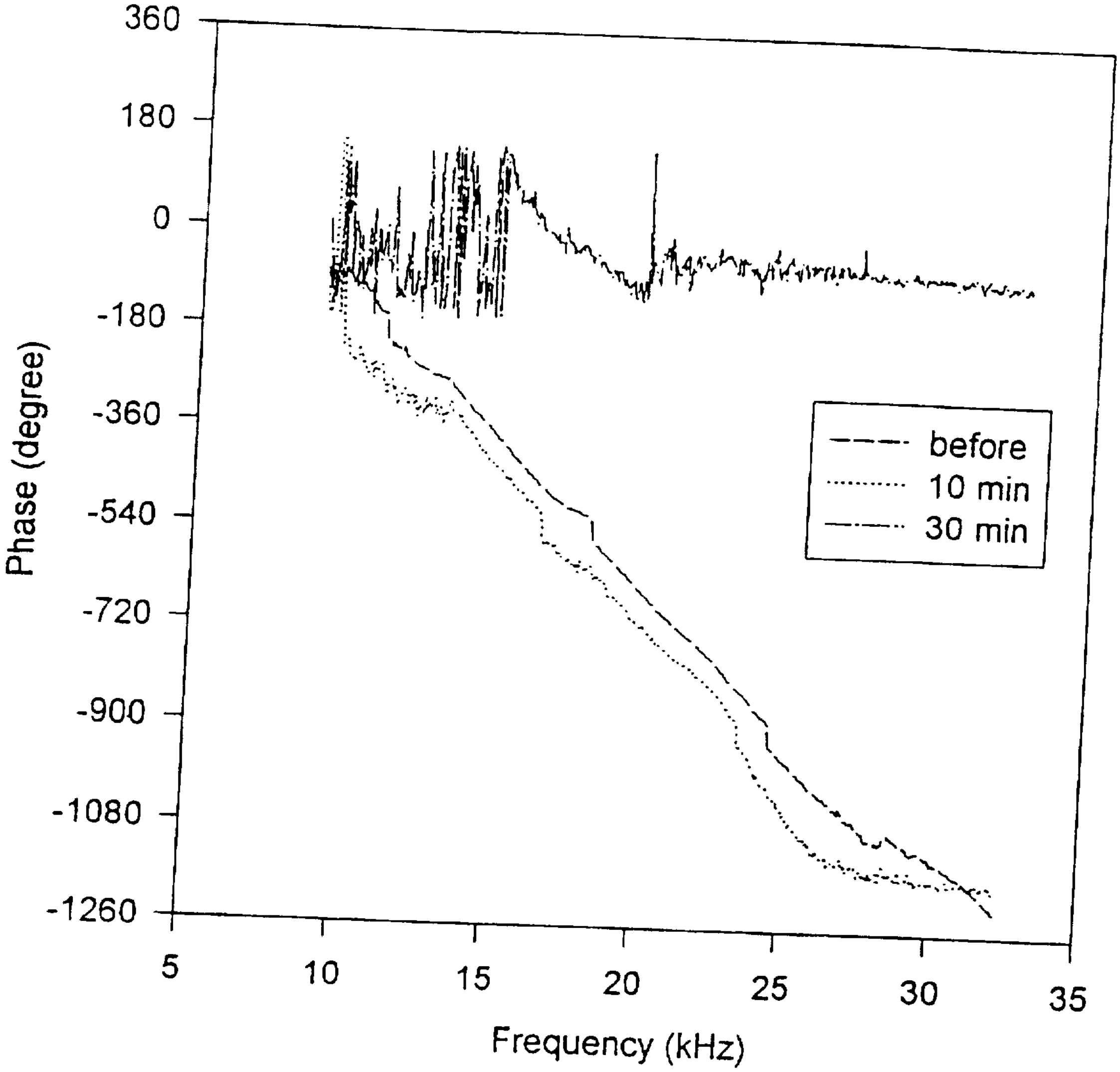
FIG. 18 is the phase response pursuant to the frequency response of FIG. 17.

An intracochlear infusion of 4% paraformaldehyde was used to completely block the EEOE. The first 10 min of the perfusion caused a dramatic decrease across all frequencies FIG. 17 and the phase curve was shifted down slightly FIG. 18. By 30 min, the EEOE amplitudes at most frequencies had already reached the noise floor and the phase curve exhibited a pattern completely different from that before the perfusion, indicating a residual electric interference signal. This interference is probably cross-talk from the electrical stimulus to the microphone due too practical difficulties in completely shielding the microphone from high intensity, high frequency currents. These results demonstrate that chemical fixation of the cochlear partition near the electrode location almost completely eliminates the EEOEs.

Amplitude responses of the EEOEs for FIGS. 10 and 11 show a linear relationship to current level similar to that found in the guinea pg cochlea. If otoacoustic emissions are proportional to hair cell displacements then this is an unexpected result, because in vitro studies show that isolated OHC motility is nonlinear. However, a system that generates linear force (sound pressure) does not necessarily have linear displacement of OHCs. The nonlinearity of OHC displacement in vitro may not be evident under the current experimental conditions, where we stimulate in the high frequency cochlear area and with limited intensities. Applicants have found, by direct measurement in vivo, that basilar membrane displacements can saturate for high current levels. Phase data in FIG. 11 indicated that the primary EEOEs were generated in the region close to the electrode and transmitted directly to the external ear canal. The cubic DP provoked by a pure tone and an electric current (that itself gives rise to the EEOE), or by two electric frequencies, demonstrated that acoustic energy from excitation of the organ of Corti by the current generates the same traveling wave along the basilar membrane as does an acoustic stimulus alone. The data indicate that electrically-provoked acoustic energy was generated by the cochlear partition near the electrode and propagated both to the ear canal and its topographic location on the basilar membrane. DPs and the EEOEs clearly show difference responses to furosemide, sodium salicylate, and in the post mortem condition. The DPs and EEOEs therefore reflect different aspects of cochlear physiology. The results imply that electromotility is essential but not sufficient for normal cochlear function.

In this study, the EEOE responses postmortem and following furosemide administration did not show the enhancement previously reported, which has provided the basis of a proposed negative feedback cochlear model. Although the current experimental conditions may be responsible for this difference, it is possible that results of previous studies showing EEOE enhancement post mortem and following furosemide administration may be due to combining the electric stimulus with a high-level acoustic stimulus. It would be interesting to explore the role of two-tone effects in these phenomena in future studies. That the EEOE responses are little changed post mortem and following furosemide, but are sensitive to sodium salicylate and fixation, further suggests that the acoustic energy of the EEOEs comes from the electromotility of the OHCs.

Our protocol provides a powerful but simple physiological method for the study of OHC motility It employs extracochlear current stimulation by a round window electrode to provoke the EEOE. The protocol is significantly different from previous studies where acoustic emissions were evoked by the intracochlear injection of alternating current into the scala media of the gerbil cochlear and the guinea pig cochlea. One important advantage of the extracochlear application of current is that the cochlea remains intact. Anther advantage is that the round window electrode can deliver more current than an intracochlear electrode. This can result in a higher sound level of emission. A higher emission level is useful to generate intermodulation DP emissions, such as the cubic DP. These advantages make it possible to study electromechanical transduction in the high frequency area of the cochlea and to explore the relationship between EEOE and normal cochlear function. Moreover, there are potential practical applications of the method; namely, evaluation of hearing loss or the development of a hearing aid. Extracochlear electric stimulation could form the basis for the development of a new type of hearing aid. A protocol such as ours can aid in the diagnosis of hearing loss and help determine the presence of functional OHCs in humans. It can also provide basic information on cochlear implant design and aid in the selection of cochlear implant patients. This is especially relevant at this time when the population of implanted patients with surviving OHCs is increasing. Patients with functioning OHCs may not require a multichannel implant, or they perhaps should receive an extracochlear implant to avoid damaging the cochlear partition by implantation.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. A method for evaluating the health of hair cells within the intact cochlea of a mammal, the method comprising:

providing a patient ear to be analyzed;

providing an electrode configured for an insertion into the patient's middle ear;

inserting the electrode into the middle ear, external of the cochlea;

positioning the inserted electrode proximate the cochlea;

applying a continuous sinusoidal electric current at a stimulation frequency to the electrode so as to excite outer hair cells within the inner ear and electrically evoke activity therefrom; and detecting electrically evoked otoacoustic emissions emitted from within the inner ear.

2. The method of claim 1 wherein positioning the inserted electrode proximate the cochlea comprises touching a round window of the cochlea.

3. The method of claims 1 wherein positioning the inserted electrode proximate the cochlea comprises positioning the inserted electrode proximate the round window.

4. The method of claim 1 wherein the electrode is inserted into the middle ear by delivering the electrode through the outer ear canal and inserting the electrode through the tympanic membrane into the middle ear.

5. The method of claim 1 further including the step of forming a hole through the tympanic membrane through which the electrode is inserted.

6. The method of claim 5 wherein the hole is formed by forcing an end of the electrode through the tympanic membrane.

7. The method of claim 5 wherein the hole is first surgically formed in the tympanic membrane after which the electrode is inserted through the hole.

8. The method of claim 1 wherein the electrode is provided by a wire electrode.

9. The method of claim 8 wherein the wire electrode is constructed and arranged to conform to the geometry of the outer ear canal and middle ear so as to facilitate navigating the electrode through the outer ear canal, tympanic membrane, and into the inner ear adjacent or onto the round window or adjacent the cochlea.

10. The method of claim 1 wherein the electrode is provided by a needle electrode.

11. The method of claim 1 including the additional steps of providing an acoustic speaker and a microphone within the outer ear canal concurrent with applying the electric current signal to the positioned electrode in order to produce and detect acoustic signals resulting from electrically evoked otoacoustic emissions from within the inner ear.

12. The method of claim 11 wherein electrically evoked activity produced within the inner ear as a result of the electric stimulus provides fluid pressure waves acting through the middle ear bones and the tympanic membrane to produce corresponding acoustic signals in the outer ear canal therefrom.

13. The method of claim 12 wherein the corresponding acoustic signals in the outer ear canal are analyzed with the microphone and a signal analyzer.

14. The method of claim 11 further including the step of applying a second signal to the tympanic membrane of the ear concurrent with applying the electric current signal so as to produce distortion products detectable within the outer ear canal for subsequent sound analysis.

15. The method of claim 14 wherein the second signal is an acoustic signal.

16. The method of claim 11 further including the step of applying a second signal to the cochlea wherein the second signal is an electric signal having a frequency different than the first signal.

17. The method of claim 14 wherein the resulting distortion products are cubic intermodulation distortion products.

18. The method of claim 14 further including the step of analyzing the distortion products with signal analysis techniques.

19. A method for evaluating the motility of hair cells within an intact mammalian cochlea comprising:

providing a patient ear to be analyzed;

providing an electrode configured for insertion into the patient's middle ear;

inserting the electrode into the middle ear;

positioning the inserted electrode proximate a round window of the ear; and applying continuous sinusoidal electric current to the electrode to excite the inner ear structure so as to produce electrically evoked otoacoustic emissions therefrom which is manifested as detectable acoustic emissions in the outer ear canal.

20. A method for evaluating the electromotility of hair cells within the intact inner ear of a mammalian cochlea, comprising:

providing a patient ear to be analyzed;

inserting an electrode into the patient's middle ear;

positioning the inserted electrode proximate a round window of the ear;

applying a continuous, distinct frequency signal to the electrode to structurally excite the inner ear and produce electrical-evoked otoacoustic emissions therefrom; and detecting the electrically-evoked otoacoustic emissions in an outer canal of the ear.

21. The method of claim 20 wherein the continuous, distinct frequency signal comprises a sinusoidal electric current signal.

* * * * *

UNITED STATES PATENT AND TRADEMARK OFFICE

CERTIFICATE OF CORRECTION

PATENT NO. : 5,776,179

DATED : July 7, 1998

INVENTOR(S) : Tianying Ren; Alfred L. Nuttall

It is certified that error appears in the above-identified patent and that said Letters Patent are hereby corrected as shown below:

Col. 2, line 58: After "nonlineary", insert --processing--.

Col. 3, line 12: Delete "individuals" and insert --individual--.

Col. 4, line 13: Before "outer", insert --an--.

Col. 4, line 49: (In description of Fig. 5) After "along", delete "the".

Col. 5, line 57: Delete "voltage-dependant" and insert --voltage-dependent--.

Col. 6, line 19, through Col. 6, line 28: Delete the paragraph return after "needle.", and continue in same paragraph with "The electrode 12 is inserted ..." through "membrane."

Col. 6, line 28: Begin new paragraph with "In all configurations, an electrical signal from a ...".

Col. 6, line 34: Delete "electrically-evoke" and insert --electrically-evoked--.

UNITED STATES PATENT AND TRADEMARK OFFICE

CERTIFICATE OF CORRECTION

PATENT NO. : 5,776,179

DATED : July 7, 1998

INVENTOR(S) : Tianying Ren; Alfred L. Nuttall

It is certified that error appears in the above-identified patent and that said Letters Patent are hereby corrected as shown below:

Col. 6, line 41: Before "the manner", insert --in--.

Col. 6, line 55: After "possible", insert --to--.

Col. 8, line 49: After "In accordance with", insert --this--.

Col. 9, line 60: After "duct of", insert --the--.

Col. 10, line 5: Delete "resonant" and insert --resonate--.

Col. 10, line 38: Delete "individuals" and insert --individual's--.

Col. 10, line 47: After "subjected", insert --to--.

Col. 12, line 14: Delete "excite" and insert --excites--.

Col. 12, line 15: Delete "produce" and insert --produces--.

Col. 12, line 17: Delete "originating".

Col. 12, line 54: Delete "where" and insert --were--.

Col. 12, line 58: Delete "principle" and insert --principal--.

UNITED STATES PATENT AND TRADEMARK OFFICE

CERTIFICATE OF CORRECTION

PATENT NO. : 5,776,179

DATED : July 7, 1998

INVENTOR(S) : Tianying Ren; Alfred L. Nuttall

It is certified that error appears in the above-identified patent and that said Letters Patent are hereby corrected as shown below:

Col. 12, line 63: Delete "applicant's" and insert --applicants--.

Col. 15, line 1: Before "FIG. 17", insert --as shown in--.

Col. 15, line 1: After "slightly", insert --as shown in--.

Col. 15, line 7: Delete "too" and insert --to--.

Col. 15, line 14: Delete "pg" and insert --pig--.

Col. 15, line 37: Delete "difference" and insert --different--.

Col. 15, line 58: Insert a period after "motility".

In the Claims:

Col. 16, line 50, Claim 3: Delete "Claims 1" and insert --Claim 1--.

Signed and Sealed this

Twelfth Day of January, 1999

*Attest:*

*Attesting Officer*

*Acting Commissioner of Patents and Trademarks*